US007125712B2

(12) United States Patent
Luo et al.

(10) Patent No.: US 7,125,712 B2
(45) Date of Patent: Oct. 24, 2006

(54) BOVINE IMMUNODEFICIENCY VIRUS (BIV) BASED VECTORS

(75) Inventors: Tianci Luo, Clarksville, MD (US); Robert David Berkowitz, San Francisco, CA (US); Michael Kaleko, Rockville, MD (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/076,498

(22) Filed: Mar. 8, 2005

(65) Prior Publication Data

US 2006/0019394 A1    Jan. 26, 2006

Related U.S. Application Data

(62) Division of application No. 09/734,836, filed on Dec. 12, 2000, now Pat. No. 6,864,085.

(60) Provisional application No. 60/249,492, filed on Nov. 17, 2000, provisional application No. 60/266,318, filed on Dec. 14, 1999.

(51) Int. Cl.
*C12N 15/63* (2006.01)
*C12N 15/87* (2006.01)
*C12N 15/00* (2006.01)
*C07H 21/00* (2006.01)
*C12P 21/06* (2006.01)
*C12P 19/34* (2006.01)
*A61K 39/00* (2006.01)

(52) U.S. Cl. .............. 435/320.1; 424/207.1; 435/5; 435/69.1; 435/91.2; 435/455; 435/456; 435/465; 536/23.4; 536/23.72; 536/24.1; 536/24.2

(58) Field of Classification Search .............. 424/207.1; 435/5, 69.1, 91.2, 320.1, 457, 456, 465; 536/23.4, 536/23.72, 24.1, 24.2
See application file for complete search history.

(56) References Cited

U.S. PATENT DOCUMENTS

| 5,112,756 A | 5/1992 | Bouillant et al. |
| 5,380,830 A | 1/1995 | Gonda |
| 5,817,491 A | 10/1998 | Yee et al. |
| 6,013,516 A | 1/2000 | Verma et al. |

FOREIGN PATENT DOCUMENTS

| WO | WO 92/14829 | 9/1992 |
| WO | WO 99/15641 | 4/1999 |

OTHER PUBLICATIONS

Bender, et al., "Evidence That the Packaging Signal of Moloney Murine Leukemia Virus Extends into the *gag* Region," J. Virol., 61(5):1639-1646 (May 1987).
Berkowitz, et al., "RNA Packaging," Current Topics in Microbiology and Immunology, 214:177-218, (1996).

Buchschacher, et al., "Human Immunodeficiency Virus Vectors for Inducible Expression of Foreign Genes," J. virol., 66(5):2731-2739 (May 1992).
Burns, et al., "Vesicular Stomatitis Virus G Glycoprotein Pseudotyped Retroviral Vectors: Concentration to Very High Titer and Efficient Gene Transfer into Mammalian and Nonmammalian *Cells,* " Proc. Natl. Scad. Sci. USA, 90:8033-8037 (Sep. 1993).
Charneau, et al., "A Second Origin of DNA Plus-Strand Synthesis Is Required for Optimal Human Immunodeficiency Virus Replication," J. Virol., 66(5):2814-2820 (May 1992).
Gonda, et al., "Characterization and Molecular Cloning of a Bovine Lentivirus Related to Human Immunodeficiency Virus," Nature, 330: (1987).
Kaye, et al., "*cis* -Acting Sequences Involved in Human Immunodeficiency Virus Type 1 RNA AD Packaging," J. Virol. 69(10):6588-6592 (Oct. 1995).
Malim, et al., "The HIV-1 *rev trans*-Activator Acts Through a Structured Target Sequence to Activate Nuclear Export of Unspliced Viral mRNA," Nature, 338:254-257 (Mar. 16, 1989).
Markowitz, et al., "A Safe Packaging Line for Gene Transfer: Separating Viral Genes on Two Different Plasmids," J. Virol., 62(4):1120-1124 (Apr. 1988).
Mitrophanous, et al., "Stable Gene Transfer to the Nervous System Using a Non-Primate Lentiviral Vector," Gene Therapy, 6:1808-1818 (1999).
Miyoshi, et al., "Development of a Self-Inactivating Lentivirus Vector," J. Virol. 72(10):8150-8157 (Oct. 1998).
Oberste, et al., "Characterization of Bovine Immunodeficiency Virus *rev* cDNAs and Identification and Subcellular Localization of the Rev Protein," J. Virol., 67(11):6395-6405 (Nov. 1993).
Pear, et al., "Production of High-Titer Helper-Free Retroviruses by Transient Transfection," Proc. Natl. Acad. Sci. USA, 90:8392-8396 (Sep. 1993).

(Continued)

*Primary Examiner*—Ulrike Winkler
(74) *Attorney, Agent, or Firm*—Bell, Boyd & Lloyd

(57) ABSTRACT

This invention pertains to BIV constructs encompassing BIV combination vectors, BIV vectors and BIV packaging vectors and particularly the invention pertains to a three vector system comprising: a) a BIV vector construct including a DNA segment from a BIV genome, a packaging sequence to package RNA into virions; a promoter operably linked to the DNA segment; and a transgene operably linked to a second promoter; b) a BIV packaging vector construct comprising a BIV DNA sequence fragment comprising at least a gag gene or pol gene of BIV; a promoter operably linked to the BIV DNA fragment; and a polyadenylation sequence located downstream of the BIV DNA fragment; and c) an expression vector construct comprising a gene encoding a viral surface protein. Also provided is a method for transferring a gene of interest into a mammalian cell.

56 Claims, 5 Drawing Sheets

OTHER PUBLICATIONS

Schwartz, et al., "Distinct RNA Sequences in the *gag* Region of Human Immunodeficiency Virus Type 1 Decrease RNA Stability and Inhibit Expression in the Absence of Rev Protein," J. Virol., 66(1):150-159 (Jan. 1992).

Yee, et al., "A General Method for the Generation of High-Titer, Pantropic Retroviral Vectors: Highly Efficient Infection of Primary Hepatocytes," Proc. Natl. Acad. Sci. USA, 91:9564-9568 (Sep. 1994).

Zhu, et al., "Phenotypic Mixing Between Human Immunodeficiency Virus and Vesicular Stomatitis Virus or Herpes Simplex Virus," J. Acq. Immune Deficiency Syndromes, 3:215-219 (1990).

Zufferey, et al., "Self-Inactivating Lentivirus Vector for Safe and Efficient In Vivo Gene Delivery," J. Virol., 72(12):9873-9880 (Dec. 1998).

Braun, et al., "Molecular Cloning of Biologically Active Proviruses of Bovine Immunodeficiency-like Virus," Virology, 167:515-523 (1988).

Charneau, et al., "HIV-1 Reverse Transcription," J. Mol. Biol., 241:651-662 (1994).

Garvey, et al., "Nucleotide Sequence and Genome Organization of Biologically Active Proviruses of the Bovine Immunodeficiency-like Virus," Virology, 175:391-409 (1990).

Naldini, et al., "In Vivo Gene Delivery and Stable Transduction of Nondividing Cells by a Lentiviral Vector," Science, 272:263-267 (Apr. 12, 1996).

Rigg, et al., "A Novel Human Amphotropic Packaging Cell Line: High Titer, Complement Resistance, and Improved Safety," Virology, 218:290-295 (1996).

Berkowitz, et al., "Construction and Molecular Analysis of Gene Transfer Systems Derived from Bovine Immunodeficiency Virus," *Journal of Virology*, 75(7):3371-3382 (Apr. 2001).

Berkowitz, et al., "Gene Transfer Systems Derived from Visna Virus: Analysis of Virus Production and Infectivity," *Virology*, 279:116-129 (2001).

Buchschacher, et al., "Development of Lentiviral Vectors for Gene Therapy for Human Diseases," *Blood*, 95(8):2499-2504 (Apr. 15, 2000).

Cullen, B.R., "Retroviruses as Model Systems for the Study of Nuclear RNA Export Pathways," *Virology*, 249:203-210 (1998).

Gonda, et al., "Bovine Immunodeficiency Virus: Molecular Biology and Virus-Host Interations," *Virus Res.*, 32:155-181 (1994).

International Search Report PCT Application No. PCT/US00/33725, dated Aug. 21, 2001.

Kalvatchev, et al., "Acquired Immune Dysfunction in Rabbits Experimentally Infected with an Infectious Molecular Clone of the Bovine Immunodeficiency Virus (BIV127)," *Viral Immunology*, 8(3):159-164 (1995).

Kim, et al., "Minimal Requirement for a Lentivirus Vector Based on Human Immunodeficiency Virus Type 1," *Journal of Virology*, 72(1):811-816 (Jan. 1998).

Mangeot, et al., "Development of Minimal Lentivirus Vectors Derived from Simian Immunodeficiency Virus (SIVmac251) and Their Use for Gene Transfer into Human Dendritic Cells," *Journal of Virology*, 74(18):8307-315 (Sep. 2000).

Sutton, et al., "Human Immunodeficiency Virus Type 1 Vectors Efficiently Transduce Human Hematopoietic Stem Cells," *Journal of Virology*, 72(7):5781-5788 (Jul. 1998).

Trono, D., "Lentiviral Vectors: Turning a Deadly Foe into a Therapeutic Agent," *Gene Therapy*, 7:20-23 (2000).

Walder, et al., "Bovine Immunodeficiency Virus in Experimentally Infected Rabbit: Tropism for Lymphoid and Nonlymphoid Tissues," *Comparative Immunology, Microbiology & Infectious Disease*, 24:1-20 (2001).

Wu, et al., "Development of a Novel Trans-Lentiviral Vector That Affords Predictable Safety," *Molecular Therapy*, 2(1):47-55 (Jul. 2000).

Yu, et al., "Inducible Human Immunodeficiency Virus Type 1 Packaging Cells Lines," *Journal of Virology*, 70(7):4530-4537 (Jul. 1996).

Soneoka, Y., et al., "A Transient Three-plasmid Expression System for the Production of High Titer Retrovial Vectors;" Nucleic Acids Research, 23(4):628-633 (1995).

Srinivasakumar, N., et al., "The Effect of Viral Regulatory Protein Expression on Gene Delivery by Human Immunodeficiency Virus Type 1 Vectors Produced in Stable Packing Cell Lines;" Journal of Virology, 71(8):5841-5848 (Aug. 1997).

|        | EXPERIMENT |    |    |    |    |
|--------|-----|-----|-----|-----|-----|
|        | #1  | #2  | #3  | #4  | #5  |
| BCCG   |     |     |     |     |     |
| BCPG   | 0   |     |     |     |     |
| BC2CG  |     |     |     |     |     |
| BC2PG  | 5   | 6   |     |     |     |
| BC2MG  |     | 29  |     |     |     |
| BC3PG  |     | 14  |     |     |     |
| BC3MG  |     | 35  | 55  |     | 68  |
| BC4MG  |     |     |     |     | 68  |
| BC3MGppt |   |     | 73  | 60  | 84  |
| BC4MGppt |   |     |     |     | 90  |
| BC3MGgag |   |     |     | 70  |     |
| BC3MGgagppt | | |     | 70  |     |
| BC3MGgagsar | | |     | 72  |     |
| BC3MGsar |   |     |     | 71  |     |
| BC3MGsarppt | | |     | 46  |     |
| HIVPG  |     |     |     | 75  |     |
| HIVMG  |     |     |     | 100 |     |

FIG. 3

PACKAGING CONSTRUCT
BH2Δψ

BIV VECTOR BACKBONE

VSV-G EXPRESSION
CONSTRUCT

BOVINE IMMUNODEFICIENCY VIRUS (BIV) BASED VECTORS

This application is a division of U.S. Ser. No. 09/734,836 filed 12 Dec. 2000 now U.S. Pat. No. 6,864,085 and claims benefit under 35 USC §119(e) of the following U.S. provisional patent applications: (1) Provisional Application No. 60/266,318, filed Dec. 14, 1999 for "Bovine Immunodeficiency Virus (BIV) Based Vectors,"; and (2) Provisional Application No. 60/249,492, filed Nov. 17, 2000 for "Bovine Immunodeficiency Virus (BIV) Based Vectors." The disclosures of these two provisional applications are incorporated herein by reference in their entirety.

BACKGROUND OF THE INVENTION

The present invention relates generally to use of recombinant viruses as vectors, and more specifically to recombinant bovine immunodeficiency virus (BIV) based vector constructs capable of expressing a desired protein in target cells.

The use of recombinant virus vectors in a variety of applications including, for example, gene therapy requires that the virus not be capable of replication in the target cells to avoid the possibility of uncontrolled virus or cell proliferation. In addition to safety, the recombinant virus vector system must be efficient and accurate.

Retroviruses have been used as vectors to mediate gene transfer into eukaryotic cells. Retroviruses are RNA viruses that include the subfamilies lentivirus, spumavirus, and oncovirus. These viruses can replicate and integrate into a host cell genome through a DNA intermediate, generally called a provirus.

The viral vectors are generally constructed such that the majority of the viral genes are deleted and replaced by a gene of interest. Most frequently the gene of interest is transcribed under the control of the viral regulatory sequences within the long terminal repeat (LTR). Alternatively, the gene of interest may be expressed under the regulation of its own internal promoter. The genes which have been deleted from the vector are generally provided by one or more helper or packaging constructs in a packaging cell line (Bender et al., J. Virol. 61: 1639–1649 (1987) and Miller et al., Biotechniques, 7:980–990 (1989)). Also see Markowitz et al., J. Virol. 62:1120–1124 (1988) wherein complementary portions of the helper construct were divided on two separate constructs. The packaging cell line may be transfected with the retroviral vector, thereby producing vector RNA that is packaged into the virus particles. These released virus particles are replication defective and can be used to deliver the retroviral vector carrying a heterologous gene of interest to target cells.

To increase safety, efficiency and accuracy of the recombinant vector systems, various improved recombinant systems have been constructed. One type of improvement includes making safer packaging cell lines that are generated by deletions in the 3' Long Terminal Repeat (LTR). Other improvements include increasing the host range by replacement of one viral env gene with that of another viral env gene, thereby creating a hybrid producer line that generates pseudotyped helper viruses. More specifically, HIV has been given an extended host cell range by pseudotyping with the unrelated viruses VSV and HSV (Zhu et al., J. AIDS, 3:215–219 (1990) and Naldini et al., Science, 272:263–267, (1996)). Further improvements have been made by the use of minimum viral coding regions in the vector. Additionally, most packaging cell lines currently in use have been transfected with separate plasmids, each containing one of the necessary coding sequences so that multiple recombination events are necessary before replication competent virus can be produced.

In contrast to vectors derived from oncoviruses, lentivirus can infect nondividing cells. This property is especially useful for in vivo gene therapy.

BIV generally does not infect human cells and, therefore, the use of a BIV genomic backbone in the vectors of the present invention overcomes difficulties of prior packaging cell lines and further provides other related advantages for improved vector construction.

SUMMARY OF THE INVENTION

In one embodiment, the invention provides a BIV combination vector construct comprising a DNA segment from a BIV genome, wherein the DNA segment comprises a gag gene, a pol gene, a segment of the env gene, and a BIV packaging sequence to package BIV RNA into virions; a promoter operably linked to the DNA segment; and a transgene operably linked to the promoter wherein the transgene is inserted into the segment of the env gene. In a preferred embodiment, a part of the interior env gene is deleted, and the transgene is inserted into the gap created by the deletion. In further embodiments, the DNA segment may include one or more of the following genes vif, vpw, vpy, rev, and tat, particularly tat and rev.

The invention also provides a BIV vector comprising a DNA segment from a BIV genome, a packaging sequence to package RNA into virions; a first promoter operably linked to the DNA segment; and a transgene operably linked to a second promoter. In one preferred embodiment, the packaging sequence is a BIV packaging sequence and the promoter is a LTR promoter or a cytomegalovirus (CMV) promoter. In a further preferred embodiment, the DNA segment also comprises a portion of a gag gene. In another embodiment, the vector includes a rev-response element (RRE).

Further provided by this invention is a BIV packaging construct comprising a BIV DNA sequence fragment including at least a gag or pol gene of BIV; and a promoter operably linked to the BIV DNA fragment. Preferably, a polyadenylation sequence is located downstream of the BIV DNA fragment. In a further embodiment, the packaging construct includes an internal ribosome binding site (IRES) and preferably includes a heterologous intron.

The invention also provides a three vector system comprising: (1) a BIV vector construct including a DNA segment from a BIV genome, a packaging sequence to package RNA into virions; a promoter operably linked to the DNA segment; and a transgene operably linked to a second promoter; (2) a BIV packaging vector construct including a BIV DNA sequence fragment including at least a gag or pol gene of BIV; a promoter operably linked to the BIV DNA fragment, and a polyadenylation sequence located downstream of the BIV DNA fragment; and (3) an expression vector including a gene encoding a viral surface protein. In one embodiment, the viral surface protein is a vesicular stomatitis virus (VSV)-G envelope glycoprotein. In a second embodiment, the DNA segment of the BIV vector construct includes a portion of a BIV gag gene. In further embodiments, the BIV vector construct includes one or more BIV genes selected from the group consisting of gag, vif, vpw, vpy, tat, rev, and env.

Further provided by this invention is a method of transferring a gene of interest to a mammalian cell obtained by transfecting a eukaryotc host cell with the three vector system as claimed and disclosed herein; culturing the transfected host cell; collecting the virions produced; and administering the virions to a mammalian cell to allow infection of the mammalian cell and transferring the gene of interest in one embodiment, the mammalian cell is located in vitro, and in another embodiment the mammalian cell is located in vivo.

The invention further provides for a two vector system, including a first vector construct comprising, a DNA segment from a BIV genome, wherein the DNA segment comprises gag and pol genes, a BIV packaging sequence to package BIV. RNA into virions, a promoter operably linked to the DNA segment, and a transgene operably linked to the promoter; and a viral surface protein expression vector. Preferably, such vector is a veslcular stomatits virus (VSV)-G envelope glycoprotein expression vector.

Further provided by this invention is a method of transferring a gene of interest to a mammalian cell by transfecting a eukaryotic host cell with the two vector system as claimed and disclosed herein; culturing the transfected host cell and collecting the virions produced; and administering the virions to a mammalian cell to allow infection of said cell and transfer of the gene of interest.

A further, particularly preferred embodiment of this invention provides a minimal BIV-based vector system. The system comprises a minimal vector construct, a minimal packaging construct, and a minimal viral surface protein expression construct. The minimal vector construct comprises a promoter linked to a first BIV R region, a BIV U5 element linked to the first BIV R region, a packaging sequence, a transgene, and a BIV U3 element linked to a second BIV R region, wherein the promoter initiates transcription of the vector. The packaging construct comprises a promoter operatively linked to a BIV gag/pol coding sequence and a polyadenylaton signal at the 3' end of the gag/pol coding sequence. The viral surface protein expression construct comprises a promoter operatively linked to a viral envelope coding sequence and a poyadenylation signal at the 3' end of the coding sequence.

This embodiment of the invention further comprises a packaging cell. The packaging cell comprises the minimal packaging construct and the minimal viral surface protein expression construct.

The addition of the minimal vector construct results in a producer cell. The producer cell produces virions that contain the vector. Infecting a cell with the virions results in the transfer of the transgene to the cell.

BRIEF DESCRIPTION OF THE DRAWINGS

FIG. 3: BIV vectors and transduction efficiencies. All vectors contain the CMV immediate-early promoter, ending in the TATA box, linked to the BIV 5' LTR starting immediately after the TATA box. BIV sequences terminate at the gag start codon (BCCG and BCPG) or approximately 510 bp into the gag coding region (all others). All vectors contain the eGFP cDNA linked to a heterologous, "internal" promoter: CMV, PGK, or MND. Some vectors contain one or more insertions between the BIV 5' segment and the internal promoter; these insertions include a potential BIV central polypurine tract (cPPT), the 5' segment of the gag gene, the beta-interferon scaffold attachment region (SAR), and the putative BIV rev-response element (RRE). Downstream of the eGFP cDNA lies the BIV 3' LTR and approximately 130 bp (BCCG and BCPG), 1.2 kb (BC2CG, BC2PG, and BC2MG) or 80 bp (all others) of adjacent env sequences. Two vectors (BC4MG and BC4MGppt) contain modified 3' LTRs in which most of the 3' LTR U3 region is replaced by the SV40 late polyadenylation signal enhancer element ("SINSV"). Transcription start sites and directions are indicated with arrows. At the bottom are depicted two HIV-1 control vectors used in a series of experiments. At the right are the transduction efficiencies of the vectors in 293T cells 3 days post-infection, using packaging construct BH2 and VSV-G, in a series of experiments. Infections from experiments numbers 3–5 are performed in the presence of an additional buffer to retard pH elevation during spinoculation. As a result, transduction efficiencies are elevated.

DETAILED DESCRIPTION OF THE INVENTION

Figure 1:
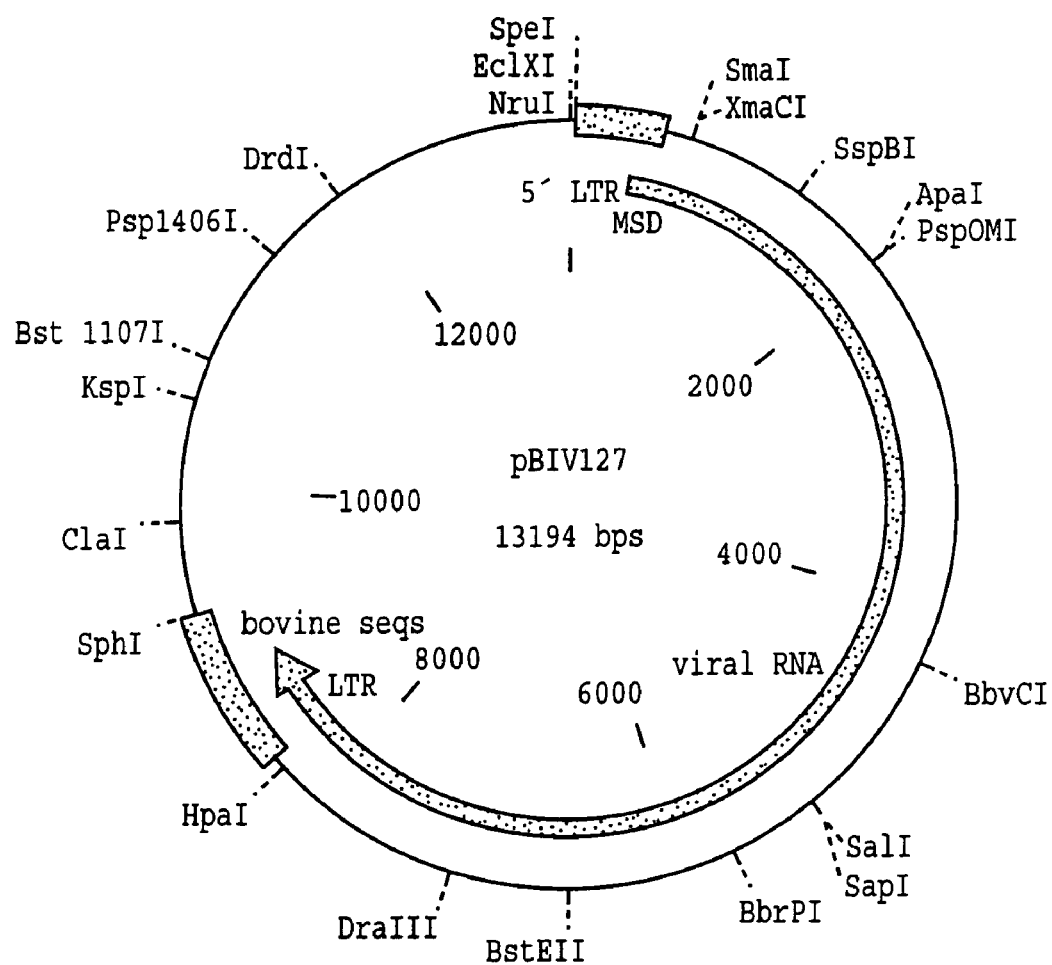
FIG. 1: Schematic illustration of wild-type BIV proviral plasmid (pBIV) clone 127.

The practice of the present invention will employ, unless otherwise indicated, conventional techniques of cell biology, molecular biology, cell culture, virology, immunology and the like which are in the skill of one in the art. These techniques are fully disclosed in current literature and reference in made specifically to Sambrook, Fritsch and Maniatis eds., "Molecular Cloning, A Laboratory Manual", $2^{nd}$ Ed., Cold Spring Harbor Laboratory Press (1989); Celis J. E. "Cell Biology, A Laboratory Handbook" Academic Press, Inc. (1994) and Bahnson et al., J. of Virol. Methods, 54:131–143 (1995).

All publications and patent applications cited in this specification are indicative of the level of skill of those skilled in the art to which this invention pertains and are hereby incorporated by reference in their entirety.

As used in this specification and claims, the singular form "a", "an" and "the" include plural references unless the context clearly dictates otherwise. For example, a virion particle includes a plurality of virion particles. Polynucleotides or nucleic acids of the invention may be in the form of RNA or in the form of DNA, which DNA includes cDNA, genomic DNA or synthetic DNA.

Bovine immunodeficiency virus (BIV) is classified in the retroviral subfamily lentivirus (Gonda et al., Nature, 330: 388–391 (1987)). Lentiviruses are exogenous, nononcogenic retroviruses and include equine infectious anemia virus (EIAV), simian immunodeficiency viruses (SIVs), visna and progressive pneumonia viruses of sheep, feline immunodeficiency virus (FIV) and human immunodeficiency viruses (HIV-1 and HIV-2). BIV has immunologic cross-reactivity with HIV, SIV and EIAV. These viruses typically contain 8,000 to 10,000 nucleotides in their genome encompassing the gag, pol and env genes, as well as long terminal repeat (LTR) sequences.

The "gag" gene is the 5'-most gene on retroviral genomes and encodes structural proteins that form the virus particle. It is translated to give a precursor polyprotein that is subsequently cleaved to yield three to five structural proteins.

The "pol" gene encodes enzymes needed for polyprotein cleavage, reverse transcription and proviral DNA integration into the chromosomes.

The "env" gene encodes the envelope proteins. As used in this disclosure, the env gene includes not only natural env gene sequences but also modifications to the env gene, including modifications that alter target specificity of retroviruses or env genes that are used to generate pseudotyped retrovirus. See PCT publication WO 92/14829, published Sep. 3, 1992, entitled "Viral Particles Having Altered Host Range."

The retroviruses share features of the replication cycle, including packaging of viral RNA into virions, infection of target cells, production of a DNA copy of the RNA genome by reverse transcription of the RNA carried in the virion to form a DNA provirus, transport of the DNA to the cell nucleus, integration of the proviral DNA into the target cell genome, transcription of mRNA from the viral DNA that is driven by a promoter within the 5' LTR sequence, translation of the gag, pol and env proteins, formation and maturation of viral particles and shedding of single membrane enveloped virions from the cell. The LTR contains cis-acting sequences important for reverse transcription, integration, transcription, and polyadenylation (Coffin J., J. Gen. Virology 42: 1–26 (1979)).

The genomes of the lentiviruses are complex. They share the above mentioned retroviral genes, gag, pol and env and in addition have a number of nonstructural/regulatory genes including a "central region" (Braun et al., J. Virol. 61:4046–4054 (1987) and Chakrabarti et al., Nature, 328: 543–547 (1987)).

The complement of nonstructural/regulatory genes found in the genomes of isolates from various species differ from one another, particularly in the env sequences. The basic genomic organization of BIV is disclosed in Garvey et al., Virology, 175:391–409 (1990) and U.S. Pat. No. 5,380,830, the disclosure of which is incorporated herein by reference in its entirety. Additionally disclosed are methods of obtaining BIV genomic DNA from BIV infected cells. The gag and pol genes are in different frames and overlap. The pol and env genes are in the same reading frame and are separated by the "central region". There are five open reading frames (ORFs) found in the central region. Three of these are similar in structure to the exons for vif, tat and rev of HIV and other lentiviruses. The other two ORFs are located in a position in the central region analogous to vpr, vpx and vpu encoding ORFs of HIV-1 and/or HIV-2. The nef ORF which is located post-env in the genomes of other lentiviruses appears to be lacking in BIV (Garvey et al., 1990 supra).

An exon is a segment of a gene. It codes for a specific part of the protein. A gene is a nucleic acid segment that is involved in producing a polypeptide chain and includes regions preceding and following the coding region segment of DNA.

The "tat" gene consists of two coding exons. The first is contained in the central region and the second in the 3' end of the env coding sequence but in a different reading frame from the env and rev exons.

The "rev" gene is also made up of two exons. The first is located near the 3' end of the central region and overlaps the 5' end of env. The second exon is found in the 3' end of env but in a different reading frame. The "rev" gene product transports intron-containing viral mRNAs, including the full length RNA used for gag-pol translation and virion packaging to the cytoplasm without splicing.

Sequences encoding BIV and plasmids containing retroviral genomes suitable for use in preparing the vector constructs of the invention may be readily obtained given the disclosure provided herein or from depositories and databases such as the American Type Culture Collection (ATCC), for example, ATCC Accession No. 68092 and ATCC Accession No. 68093 and GENBANK. Various BIV clones are disclosed in Garvey et al., supra and in U.S. Pat. No. 5,380,830. Particular reference is made to BIV 127 and 106, having ATCC Accession Nos. 68092 and 68093, respectively.

It will be understood that for the nucleotide sequence of the BIV genome, natural variations can exist between individual BIV viruses. These variations may result in deletions, substitutions, insertions, inversions or additions of one or more nucleotides as long as the claimed function of the gene is not lost. The DNA sequences encoding such variants may be created by standard cloning methods or polymerase chain reaction (PCR) U.S. Pat. Nos. 4,683,195 and 4,683,202.

The present invention provides a nucleic acid segment from a BIV genome obtainable from any strain or clone of BIV. In one embodiment, a BIV vector construct of the invention should include a sufficient number of nucleotides corresponding to nucleotides of the BIV genome to express one or more functional BIV genes.

A "BIV combination vector construct" refers to an assembly which is capable of directing the expression of a nucleotide sequence and includes a 5' LTR region having a promoter sequence region which is capable of initiating transcription of BIV; BIV gag and pol genes operably linked to the promoter; a segment of the BIV env coding region; a BIV packaging sequence; and a transgene operably linked to a promoter and inserted into the segment of the env coding region. Preferably, the transgene is operably linked to a second promoter which may be the same or different from the promoter operably linked to the BIV gag and pol genes.

The BIV env gene found in BIV clone 127 is approximately 2711 nucleotides long and starts at about nucleotide 5415. In a preferred embodiment, a transgene is inserted into the interior region of the env gene. For example the transgene may be inserted into the segment of the env coding region after the tat and rev coding exon 1 segments and before the tat and rev coding exon 2 segments. Preferably, the transgene is inserted after nucleotide 860 of the env coding segment which corresponds to BIV polynucleotide 6275. In another embodiment, a section of the env coding region is deleted. Preferably, the deleted section is from the interior region of the env gene and the transgene is inserted in the gap created by the deletion. The deleted section of the env coding region may be as short as 20 nucleotides but may be as long as 1500 nucleotides. Methods of deleting a section of the env gene are well known by those of ordinary skill in the art.

A "BIV vector construct" refers to an assembly which is capable of directing the expression of a nucleotide sequence. The vector construct should include a 5' sequence (comprising a promoter region) which is capable of initiating transcription of BIV; a DNA segment from a BIV genome; a packaging sequence from a BIV or other lentivirus or retrovirus; and a transgene operably linked to a second promoter. Accordingly, in one aspect the present invention provides a BIV vector construct comprising: a DNA segment from a BIV genome, a packaging sequence for packaging RNA into virions, a first promoter operably linked to the DNA segment, and a transgene operably linked to a second promoter. In a preferred embodiment, the packaging sequence of the BIV vector construct is a BIV packaging sequence.

A portion of a BIV gag gene may be incorporated into the DNA segment. The BIV gag gene is approximately 1431 nucleotides. Preferably, the portion of the gag gene will include no more than about 200 nucleotides. The DNA segment may further comprise a BIV gene selected from the group consisting of vif, vpw, vpy, tat, rev, and env.

In another preferred embodiment, the transgene is operably linked to a CMV promoter, a PGK promoter, or a MND promoter. The BIV vector construct may further comprise one or more of a rev response element (RRE), a interferon-beta scaffold attachment region (SAR), which preferredly is of human origin, and/or a central polypurine tract, which preferredly are located between the BIV 5' segment and the internal ("second") promoter. Thus, in one preferred embodiment, the transgene operably linked to a second promoter is located downstream of the putative BIV RRE.

In yet another preferred embodiment, the BIV vector construct of the invention is a self-inactivating vector. In particular, a portion of the U3 region of the 3' LTR of the BIV vector construct may be deleted or replaced by a heterologous sequence. Preferred is the replacement of a portion of the U3 region of the 3' LTR by the SV40 late polyadenylation signal enhancer element.

In a particularly preferred embodiment, the BIV vector construct is a self-inactivating vector and further includes a transgene which is operably linked to a MND promoter and comprises a RRE and a central polypurine tract (cPPT) upstream of the MND promoter.

A "BIV packaging construct," also sometimes referred to as a helper construct, refers to an assembly which is capable of directing expression of a nucleotide sequence wherein the nucleotide sequence includes at least the gag gene or pol gene of BIV, a promoter operably linked to the nucleotide sequence, and a pblyadenylation sequence located downstream of the nucleotide sequence encoding the gag or pol genes. Preferably, the polyadenylation sequence is derived from Simian virus 40 (SV40).

The BIV vector construct, BIV combination vector construct, and the BIV packaging construct discussed above may include other BIV genes in addition to the specific genes mentioned above. Other genes include pol, vif, vpw, vpy, tat, rev, and env genes. Particularly the BIV constructs would include nucleotides corresponding to a functional BIV rev gene. However, the BIV constructs may include a rev gene obtained from a different lentivirus and particularly an HIV rev gene. The BIV constructs of the invention may also include a nuclear export element, preferably a rev response element (RRE), preferably downstream of the transgene insert. The RRE may be from a lentivirus other than BIV. Preferably, the BIV constructs would also include a sufficient number of nucleotides corresponding to a functional tat gene. The 3' LTR of the BIV genome may also be included as described below.

In another embodiment, the present invention envisages a method of producing a packaging cell line which includes transforming, preferably transfecting an established cell line with the BIV combination vector construct or with a BIV packaging construct as disclosed above. For gene therapy applications, it is necessary to generate large volume of supernatants which can not be easily prepared by transient transfection. Therefore producer cell lines may be used to transfer genes of interest to a target cell. A producer cell line refers to a cell line which is capable of producing recombinant BIV particles. The producer cell line should include an integrated BIV construct as disclosed above. A number of BIV vectors may be contained within the recombinant BIV particle, including the BIV constructs of the present invention. Various methods are known in the art to identify retroviral packaging cells capable of producing recombinant viral vector particles. These methods include ELISA and Western Blot.

Non-limiting examples of packaging cells lines include PA12, PA317, FLYA13, PE501, PG13, CRIP, RD114, GP7C-tTA-G10, PPA-6, and PT67 (Miller et al., Mol. Cell. Biol. 6:2895 (1986); Miller et al., Biotechniques 7:980 (1989); Danos et al., Proc. Natl. Acad. Sci. USA 85:6460 (1988); Pear et al., Proc. Natl. Acad. Sci. USA 90:8392 (1993) and Rigg et al., Virol. 218:290 (1996).

In an alternative preferred embodiment, the invention provides a minimal vector construct. The vector construct comprises a promoter linked to a first BIV R region, a BIV U5 element linked to the first BIV R region, a packaging sequence, a transgene, and a BIV U3 element linked to a second BIV R region, wherein the promoter initiates RNA transcription of the vector. Preferably, the packaging sequence is a BIV packaging sequence. Alternatively, it may be from another lentivirus or retrovirus. In addition, it is preferred that any start codons in the packaging sequence be eliminated by deletion or mutation. It is also preferred that the major splice donor site be inactivated or eliminated. These changes to the packaging sequence and the splice donor site are accomplished by standard techniques.

In a particularly preferred aspect of the minimal vector, one or more sequences in the U3 element are mutated or deleted in order to diminish or eliminate U3-mediated transcription of any downstream genes. This provides for a self-inactivating vector. In such a situation, the transgene is operably linked to an internal promoter. In addition, it is preferred that the U3 element further contain a sequence that enhances polyadenylation. A preferred example is the SV40 late polyadenylation signal upstream enhancer element (Sehet, et al., Mol. Cell Biol., 12:5386–5393 (1992)).

The minimal vector may contain additional elements. One such element is a cPPT. Preferably, the cPPT is a BIV cPPT. The vector may also further comprise a 3' polypurine tract, which is located immediately upstream (i.e., 5') of the 3' U3 element.

In addition, the vector may comprise an RNA transport element. Such transport element may be a lentiviral RRE. Preferably, the lentiviral RRE is a BIV RRE. Alternatively, the RNA transport element is a constitutive transport element (CTE). Most preferably, the CTE is a Mason-Pfizer Monkey Virus CTE. An alternatively preferred CTE is an Avian Leukemia Virus CTE.

In an alternative preferred embodiment, the invention also provides a minimal packaging construct. The construct comprises a promoter operatively linked to a BIV gag/pol coding sequence and a polyadenylation signal at the 3' end of the gag/pol coding sequence. Preferably, the packaging construct further contains a heterologous intron upstream (i.e., 5') of the gag/pol coding sequence. In addition, the packaging construct may contain an RNA transport element.

That element may be a lentiviral RRE, preferably a BIV RRE, or it may be a CTE as described above. The packaging construct may also contain a Rev coding sequence.

A heterologous intron may be included in the constructs, and particularly in the packaging constructs. Heterologous introns are known and non-limiting examples include the human beta-globin gene intron. Introns used in the constructs of the invention may be obtained from the SV40 virus and the human insulin gene. Preferably, the intron will be located upstream of the gag and pol nucleotide sequences.

In further embodiments, the constructs of the invention may include an internal ribosome binding site (IRES), which allows translation of a second gene, preferably a heterologous gene. The heterologous gene may be a marker gene or a gene encoding a protein of interest as further disclosed below.

A requirement for the expression of a BIV gene or a transgene is an adequate promoter operably linked to the coding nucleic acid sequence. The term "operably linked" refers to an arrangement of elements wherein the components are configured so as to perform their usual or expected function. The promoter or other control elements need not be contiguous with the coding sequence. There may be intervening residues between a promoter or control elements and the coding region so long as the functional relationship is maintained.

With respect to the constructs as disclosed herein, the choice of promoter is well within the skill of one in the art and extends to any eukaryotic, prokaryotic, or viral promoter capable of directing gene transcription in a target or host cell transformed with a construct according to the invention. The promoter may be a tissue specific promoter, inducible promoter, synthetic promoter or hybrid promoter. More than one promoter may be placed in the constructs of the invention. Preferably, the BIV genes will be operably linked to one promoter and the transgene insert will be operably linked to a second promoter. Examples of promoters useful in the constructs of the invention include, but are not limited to, phage lambda (PL) promoter, SV40 early promoter, a herpes simplex viral (HSV) promoter; a cytomegalovirus (CMV) promoter, such as the human CMV immediate early promoter; tetracycline-controlled trans-activator-responsive promoter (tet) system; a long terminal repeat (LTR) promoter, such as a MoMLV LTR or an HIV LTR; the U3 region promoter of Moloney murine sarcoma virus; Granzyme A promoter; regulatory sequences of the metallothionin gene; CD34 promoter; CD8 promoter; thymidine kinase (TK) promoter; B19 parovirus promoter; PGK promoter; glucocorticoid promoters; heat shock protein (HSP) promoters, such as HSP65 and HSP70 promoters; immunglobulin promoters; MMTV promoter; rous sarcoma virus (RSV) promoter; lac promoter; CaMV 35S promoters; and nopline synthetase promoter. Numerous promoters are available from commercial sources such as Stratagene (La Jolla, Calif.).

Preferred promoters include the promoter region of the LTRs, such as the 5' LTR promoter of HIV or BIV. Additionally preferred promoters include CMV promoters and PGK promoters. Particularly preferred is the MND promoter. Various other control sequences may also be incorporated into the constructs of the invention, for example enhancers and scaffold attachment regions (SARs). Particularly preferred is the scaffold attachment region derived from human interferon-beta. Particular enhancer sequences can readily be determined by one of ordinary skill in the art.

A "packaging sequence" is defined as sequences necessary for packaging retroviral RNA into virions. The packaging sequences are generally located in the region between the 5' major splice donor and the gag gene initiation codon. While a BIV derived packaging sequence is preferred, the vectors according to the invention may include packaging sequences corresponding to other retroviruses, particularly lentiviruses, and more particularly corresponding to HIV-1, HIV-2 or SIV. The packaging sequences may include as many as 1000 nucleotides or a few as 50 nucleotides. The size of a packaging sequence region can be determined by one of ordinary skill in the art.

As disclosed above, one or more constructs according to the invention may further include a polyadenylation signal (polyA) that is positioned 3' of the coding sequence. The polyA tail may be of any size which is sufficient to promote stability in the cytoplasm. The polyA may be derived from a lentivirus such as BIV, HIV, and SIV. However, the polyA sequence may be derived from other viruses as well, such as the SV40 polyA.

In addition to the promoter region, the long terminal repeats (LTR) of retroviruses contain cis-acting elements that are important for reverse transcription, integration, transcription and polyadenylation, and one or more of these elements may be incorporated into the constructs of the invention. Preferably, the constructs comprise nucleotides corresponding to a sufficient number of nucleotides of a BIV LTR at the 5' end to result in a functional LTR. The constructs may also include a 3' LTR region. The proviral LTR of BIV 127 is 589 polynucleotides. The LTR is comprised of U3, R, and U5 elements. (U.S. Pat. No. 5,380,830)

The invention further encompasses two and three vector systems including the BIV vector construct, the BIV combination vector construct, and the BIV packaging construct. In one embodiment, the three vector system will comprise the BIV vector construct and the BIV packaging vector construct as defined above and further a third construct. The third construct is an expression vector construct comprising a gene encoding a viral surface protein from a different virus. The viral surface protein may be any other viral envelope protein, including vesicular stomatitis virus envelope glycoprotein (VSV-G), MoMLV env protein, or envelopes derived from Gibbon Ape Leukemia virus (GaLV), Rhabdoviride (Rabies, Mokola, Lyssa), Alphaviruses (Ross River virus, Sindbis), Paramyvovirus (Sendai) Filovirus (Ebola, Marburg), Retroviruses (MLV, 10A1, Xeno) Arenaviruses (LCMV), Parainfluenza virus. In a preferred embodiment the surface protein is a VSV-G. (Burns et al., PNAS, 90:8033–8037 (1993) and Yee et al., PNAS 91:9564–9568 (1994)). See also U.S. Pat. No. 5,817,491, issued Oct. 6, 1998, the disclosure of which is incorporated herein by reference in its entirety.

A two-vector system may include the BIV combination vector construct according to the invention and the surface protein expression vector as disclosed above. In a preferred embodiment the surface protein vector construct is a vesicular stomatitis virus (VSV-G) envelope glycoprotein expression vector.

The titer of VSV-G-pseudotyped BIV virus preparations can be increased by centrifugation of the virus. An unconcentrated VSV-G-pseudotyped BIV virus preparations may possess a titer of approximately $5\times10^5$ infectious units (IU) per ml in the human kidney epithelial cell line 293T. With virus concentration, the titer can be raised significantly.

Generally, the titer of the vectors of the invention can be increased by, first, collecting the virus particles via centrifugation of the virus-containing medium, second, removing the supernatant, and, third, suspending the virus particles in a small volume of fresh medium. For example, concentating the virus 10-fold by suspending the collected virus in a volume of liquid 10-fold smaller than the original volume before centrifugation, results in 3–10-fold increases in the transduction efficiency. As the person skilled in the art will readily appreciate, a further concentration of the virus will result in even higher increases in transduction efficiency.

The BIV based constructs according to the invention used alone or in combination may be used to transform virtually any cell line or host cell. Eucaryotic host cells are preferred. Transformation may be by transfection or transduction. Transfection is the transformation of target or host cells with isolated DNA genomes. Reference is made to Kriegler, M., Gene Transfer and Expression: A Laboratory Manual, W. H. Freman & Company NY (1990). Methods of transduction include direct co-culture of cells with producer cells (Bregni et al., Blood 80:1418–1422 (1992) or culturing with viral supernatant alone or with or appropriate growth factors (Xu et al., Exp. Hemat., 22:223–230 (1994). Reference is also made to commercially available kits, such as CalPhos kit, (Clontech Inc. Palo Alto, Calif.) and Profection kit, (Promega, Madison Wis.) See Kotani et al., Human Gene Ther. 5:19–28 (1994) and Forstell et al., J. Virol. Methods 60:171–178 (1996) for methods of spinoculation.

Once a cell line is transfected or transduced with the constructs of the invention, genes will be expressed and new virions will be made by the cell. As a result, the virions may be collected and used to infect a target cell, thereby transferring the gene or genes of interest in the vector to the target cell.

Preferably, the cells are mammalian cells; most preferably, they are primate cells, especially human cells. Examples include human embryonic kidney cells (293T), EREp rabbit cells, Cf2Th (ATCC No. CRL 1430), CHO, SW480, CV-1, the human T cell line CEM-SS, Jurkat, the MDCK and D17 dog cell line, HT1090, LINA, WES and murine cell line NIH3T3. A cell line or cell culture denotes eukaryotic cells grown or maintained in vitro. It is understood that descendants of a cell may not be completely identical (either morphologically, genotypically or phentotypically) to the parent cell.

In a particularly preferred embodiment of the invention, the minimal vector and packaging constructs are used to make packaging cells and producer cells. The packaging cell comprises the packaging construct of the invention and a minimal viral surface protein expression construct. The latter construct comprises a promoter operatively linked to a viral envelope coding sequence and a polyadenylation signal at the 3' end of the coding sequence. The construct may further comprise a heterologous intron between the promoter and the coding sequence. The viral envelope is any one of those previously described herein. Preferably, it is the VSV-G. virus envelope.

The packaging cell is transfected with the minimal vector construct to make a producer cell. The producer cell comprises: (i) a BIV gag/pol coding sequence; (ii) a viral envelope coding sequence; and (iii) a vector construct comprising a promoter linked to a first BIV R region, a BIV U5 element linked to the first BIV R region, a packaging sequence, a transgene, and a BIV U3 element linked to a second BIV R region. The producer cell is cultured, and it produces virions containing the minimal vector of the invention. This minimal vector is the RNA version of the minimal vector construct and does not contain the promoter linked to the first BIV R region. Preferably, the RNA vector further comprises an internal promoter, as described herein, operably linked to the transgene. Most preferably, such vector is a SIN vector as described herein. The virions are used to infect desired target cells, thereby transferring the transgene to the target cell.

A number of target cells, including cell lines and primary cells of human and nonhuman origin, are successfully infected with the vectors of the invention. These include the dog osteosarcoma cell line D-17, the rat smooth muscle cell line A-10, the mouse neuronal cell line MN9D, the human endothelial cell line HUVEC, rat primary endothelial cells, human primary lymphocytes and human primary hematopoetic stem cells. The latter two cell types are comprised mostly of non-dividing cells. Accordingly, the vectors of the present invention are particularly useful to infect non-dividing primary human cells. For example, the vectors of the invention can infect the HUVEC cell line after gamma-irradiation to such an extent that proliferation of the cells was abrogated. After such gamma-irradiation, the results are similar to those before gamma-irradiation.

Preferred target or host cells are mammalian cells, preferably primate cells, and most preferably human cells. Preferred human cells include hematopoietic cells. Hematopoietic cells encompass hematopoietic stem cells, erythrocytes, neutrophils, monocytes, platelets, mast cells, eosinophils, basophils, B and T lymphocytes. Hematopoietic stem cells and T-cells are especially preferred.

Prior to transfection or transduction, hematopoietic cells may be isolated and selected. Methods for isolating and selecting cells are well known in the art (U.S. Pat. Nos. 5,061,620; 5,677,136 and 5,750,397). For example sorted $CD34^+Thy-1^+Lin^-$ cells from either adult bone marrow (ABM) or mobilized peripheral blood (MPB) are used. $CD34^+Thy-1^+Lin^-$ are highly enriched in human hematopoietic stem cells and can be isolated from ABM and MPB by flow cytometry (U.S. Pat. No. 5,061,620).

The present invention also relates to a method of transferring a gene of interest to a mammalian cell comprising: transfecting a eukaryotic host cell with the two or three vector system as disclosed above; culturing the transfected host cell; collecting the virions produced; and administering the collected virions to a mammalian cell to allow infection of the mammalian cell and thereby transferring the gene of interest.

As disclosed above, methods of transfecting host cells are known and further reference is made to Graham and van der Eb, Virology 52:456–467, 1973.

Methods of culturing transfected and transduced cells are well known and reference is made to Freshney, R. I. "Culture of Animal Cells, A Manual of Basic Techniques", Wiley-Liss Inc. (1994). Various culture media are commercially available and non-limiting examples include DMEM, IMDM, X-vivo 15 and RPMI-1640. The formulations may be supplemented with a variety of different nutrients and growth factors. For culturing $CD34^+$ hematopoietic stem cells or progenitor cells, cytokines are preferably combined in the media. These cytokines include but are not limited to IL-6, TPO, SCF, IL-3 and LIF. Methods of administering cells are well known, and these methods include administration to human patients for gene therapy.

Methods of collecting virions produced by transfected cells are described, for example, in Rigg et al., Virology 218:290–295. The virions, which include the BIV based constructs of the present invention, may be administered in vivo or in vitro to mammalian cells. Additionally, it is preferred that the virion includes a heterologous therapeutic gene as disclosed herein. The virions produced according to the invention by use of the BIV based constructs are recombinant particles or virions. A "recombinant BIV particle or virion" refers to a virus particle that contains a BIV based vector RNA according to the invention. In some instances, the BIV vector construct may be contained in a particle derived from viruses other than BIV, for example other retroviruses and particularly other lentiviruses.

As used herein, the gene of interest generally referred to as a transgene is a heterologous gene, for example a marker gene. The choice of a marker gene is within the skill of those in the art, and non-limiting examples include, drug resistant markers, such as the (Neo$^r$) gene which encodes neomycin phosphotransferase; the HSV-tk gene, resulting in cells sensitive to agents such as acyclovir and gancyclovir; low-affinity nerve growth factor receptor (NGFR); enhanced green fluorescent protein (eGFP); enhanced yellow fluorescent protein; dihydrofolate reductase gene (DHFR); the bacterial hisD gene; murine CD24 (HSA); murine CD8a (lyt); bacterial genes which confer resistance to puromycin, phleomycin or beta-glactosidase (such as the lacZ gene); and a glutamine synthetase (GS) gene. In one preferred embodiment the marker gene is eGFP. The marker gene is preferably under the control of a separate promoter that will allow identification of target cells containing the marker gene.

A wide variety of nucleotide sequences generally referred to as transgenes may be carried by a BIV based construct of the present invention, in addition to or alternatively in the absence of a marker gene. Preferably, the nucleotide sequences should be of sufficient size to allow production of viable virus particles. A non-exhaustive list of these transgenes (heterologous genes) includes sequences which encode proteins, antigens, ribozymes, as well as antisense sequences.

The protein may be a therapeutic protein or a structural protein. Further the protein may be the entire protein or only the functionally active fragment thereof. The protein may include, for example, one that regulates cell differentiation or a therapeutic gene capable of compensating for a deficiency in a patient that arises from a defective endogenous gene. The therapeutic gene may be one that antagonizes production or function of an infectious agent, antagonizes pathological processes, improves a host's genetic makeup or facilitates engraftment.

Specific examples of therapeutic genes or gene sequences are ones effective in the treatment of adenosine deaminase deficiency (ADA); sickle cell anemia, recombinase deficiency, recombinase regulatory gene deficiency, HIV such as an antisense or transdominant REV gene, or gene carrying herpes simplex virus thymidine kinase (HSV-tk). The therapeutic gene may be a non-human gene, for example a yeast gene (Seo et al., Proc. Natl. Acad. Sci. 95:9167(1998)).

Nucleotide sequences for the transgenes may be obtained from various databases such as GENBANK and from commercial sources such as Advanced Biotechnologies (MD). Additionally cDNA sequences that encode for the heterologous sequence may be obtained from cells which express or contain the sequence by methods well known in the art, utilizing for example PCR.

Additionally the gene of interest may be selected from DNA sequences encoding tumor necrosis factor genes, such as TNF-α; genes encoding interferons such as interferon-α, interferon-β, and interferon-γ; genes encoding interleukins such as IL-1, IL-1β, and interleukins 2 through 14, in particular IL-2, IL4, IL-6 and IL-10; genes encoding GM-CSF or G-CSF; genes encoding adenosine deaminase, or ADA; genes which encode cellular growth factors, such as lymphokines, which are growth factors for lymphocytes; genes encoding soluble CD4; Factor VIII; Factor IX; T-cell receptors; the LDL receptor, ApoE, ApoC,ApoI and other genes involved in cholesterol transport and metabolism; the alpha-1 antitrypsin gene, the ornithine transcarbamylase gene, the CFTR gene, the insulin gene, the NDI-1 gene, negative selective markers or "suicide" genes, such as viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, and antisense sequences which inhibit viral replication. Antisense sequences are designed to bind RNA transcripts and thereby prevent cellular synthesis of a particular protein or prevent use of that RNA sequence by the cell.

For human patients, a therapeutic gene will generally be of human origin although genes of closely related species that exhibit high homology and biologically identical or equivalent function in humans may be used if the gene does not produce an adverse immune reaction in the recipient. A therapeutic active amount of a nucleic acid sequence or a therapeutic gene is an amount effective at dosages and for a period of time necessary to achieve the desired result. This amount may vary according to various factors including but not limited to sex, age, weight of a subject, and the like.

Methods known in the art may be used to assay the expression of a transgene in the target cell. These methods include flow cytometry selection, protein detection by western blot analysis, use of PCR (U.S. Pat. Nos. 4,683,195 and 4,683,202), nucleotide selection by northern or southern blots, and enzyme immunoassays, Sambrook J, Fritsch E F, Maniatis T. Molecular Cloning: A Laboratory Manual Cold Spring Harbor Laboratory: Cold Spring Harbor, N.Y., 1989.

EXAMPLES

Example 1

Materials and Methods

Example 1.1

Construction of Plasmids

Vectors are generated differing in (i) the amount of gag and env sequences (BC vs. BC2 prefix); (ii) the internal promoter driving eGFP expression: CMV (CG suffix) vs. PGK (phosphoglycerate kinase promoter (1); PG suffix) vs. MND (myeloid proliferative sarcoma virus promoter (Robbins, P. B., X. J. Yu, D. M. Skelton, K. A. Pepper, R. M. Wasserman, L. Zhu, and D. B. Kohn. 1997. J Virol. 71:9466–9474); MG suffix); (iii) the placement of eGFP within the vector (i.e. upstream or downstream of the putative BIV RRE; BC2 vs. BC3 prefix); and (iv) additional segments inserted downstream of the putative BIV packaging signal (gag, ppt, sar suffixes). In addition, two vectors contain a modified 3' LTR in which a large portion of U3 (including the TATA box) is replaced by a small SV40 virus segment containing the late polyadenlyation signal upstream enhancer element (USE; Schek, N., C. Cooke, and J. C. Alwine. 1992. Mol Cell Biol. 12:5386–5393; BC3 vs. BC4 prefix).

All restriction endonucleases are purchased from Roche Molecular Biochemicals (Indianapolis, Ind.). Plasmid pBIV, containing BIV proviral clone 127 (Garvey, K. J., M. S. Oberste, J. E. Elser, M. J. Braun, and M. A. Gonda. 1990. Virology. 175:391–409), is obtained from the National Institutes of Health.

Plasmid pCI is obtained from Promega (Madison, Wis.). Plasmid pCIGL contains the vesicular stomatitis virus glycoprotein (VSV-G) cDNA (Burns, J. C., T. Friedmann, W. Driever, M. Burrascano, and J. K. Yee. 1993. Proc Natl Acad Sci USA. 90:8033–8037, Yee, J. K., A. Miyanohara, P. Laporte, K. Bouic, J. C. Burns, and T. Friedmann. 1994. Proc Natl Acad Sci USA. 91:9564–9568) in the pCI polylinker, downstream of the human cytomegalovirus (CMV) immediate-early promoter and chimeric intron and upstream of the simian virus 40 (SV40) late polyadenylation signal.

Plasmid pCrev, containing the HIV-1 rev cDNA under control of the CMV promoter, has been described previously (Malim, M. H., J. Hauber, R. Fenrick, and B. R. Cullen. 1988. Nature. 335:181–183).

Plasmid pBH1 is generated by sequential insertion of two pBIV segments into the pCI polylinker using standard techniques: a 5.5 kb SmaI-XbaI fragment containing the gag, pol, vif, vpw, and vpy genes, as well as the first coding exons of the tat and rev genes; and a 1.3 kb DraIII-PvuII fragment containing the putative rev-response element (RRE) and the second coding exons of the tat and rev genes.

Plasmids pBH2 and pBH3 are constructed in the same way, but the chimeric intron is deleted; moreover, the pBH2 5' BIV fragment also contains the 3' 70 bp of the leader, including the major splice donor site.

Plasmids pBH1 and pBH3 are also modified by insertion of (1) an approx. 500 bp fragment of HIV-1 containing the RRE, (2) an internal ribosome entry site (IRES) from encephalomyocarditis virus (Jang, S. K., M. V. Davies, R. J. Kaufman, and E. Wimmer. 1989. J Virol. 63:1651–1660), and (3) the puromycin N-acetyltransferase cDNA (Vara, J. A., A. Portela, J. Ortin, and A. Jimenez. 1986. Nuc Acids Res. 14:4617–4624).

Plasmid pBBB is generated by digesting plasmid pBIV with BfrI and BgIII to remove most of the coding region and inserting into the gap a short polylinker created by annealing oligonudeotides BB5 (5'-TTAAGATTTAAATACGCGT-GCGGCCGCA-3') and BB3 (5'-GATCTGCGGCCG-CACGCGTATTTAAATC-3').

Packaging construct BH2 and an HIV-1 packaging construct (the HIV packaging construct begins with the CMV promoter, followed by a heterologous intron, the HIV major splice donor, the entire HIV coding region except for deletions in vpu, env and nef, then the HIV-1 RRE and finally the SV40 polyadenylation site, see also Douglas, J., W.-Y. Lin, M. Panis, and G. Veres. Human Gene Therapy, "Efficient HIV-based vector transduction of unstimulated human CD34+ cells in the SCID-hu Thy/Liv model of human T cell lymphopoiesis.") are each modified by insertion of two hemagglutinin (HA) oligonucleotides immediately upstream of the gag stop codon and deletion of most of the pol coding region as follows. First, a small fragment containing the gag stop codon of each packaging construct (290 bp ApaI-AccI fragment of BIV, 360 bp ApaI-BstXI fragment of HIV-1) is ligated to ApaI/EcoRV-digested pBluescriptSK+ (Stratagene, La Jolla Calif.). Next, each subclone is subjected to reverse PCR amplification using primers containing the HA tags: HHAS 5'-TATCCATACGATGTTCCAGATTATGCT-TAAAGATAGGGGGGCAATTAAAG-3' and HHAA 5'-AGCATAATCTGGAACATCGTATGGATAT-TGTGACGAGGGGTCGCTG-3' for HIV-1 and BHAS 5'-TATCCATACGATGTTCCAGATTATGCT-TAGACAAACAGCCTTTTATAAAG-3' and BHAA 5'-AG-CATAATCTGGAACATCGTATG-GATAATCTAATATAAGAGGGGGTGC-3' for BIV. Each PCR product is circularized, then the modified gag fragment is excised with ApaI/SmaI and ligated to the parental packaging construct deleted between the ApaI site in gag and the 3' end of pol (Asp718 for HIV-1, NsiI for BIV).

The CMV immediate-early enhancer/promoter is used to replace the BIV promoter in the 5' LTR in plasmids pBIV and pBBB as follows. First, the CMV region upstream of the TATA box is subjected to PCR amplification with primers CB5 (5'-CGGGATCCCGTAGTTATTAATAGTAAT-CAATTACGG-3') and CMVBIV3 (5'-AGATATGGTT-TATATAGACCTCCCACCGTACA-3') while the BIV region downstream of the TATA box is subjected to PCR amplification with primers CMVBIV5 (5'-GGGAGGTC-TATATAAACCATATCTTCACTCTGT-3') and Bgag3 (5'-GCCGTTTCTGTACTCTCTGGT-3'). Second, the two amplified products are mixed and subjected to amplification using primers CB5 and Bgag3. The final product is digested with XmaCI and ligated to plasmids pBIV and pBBB previously digested with NruI and XmaCI, generating plasmids pBIVC and pBBBC.

Plasmid pBIVC is then digested with SmaI and AflIII to remove most of the coding region and blunt end-ligated to a DNA segment containing either the CMV promoter or the mouse phosphoglycerate kinase (PGK) promoter (Adra, C. N., P. H. Boer, and M. W. McBurney. 1987. Gene. 60:65–74) linked to the enhanced green fluorescent protein (eGFP) cDNA (Promega, Madison Wis.), generating plasmids pBCCG (also named pBIVC-SACG) and pBCPG (also named pBIVC-SAPG), respectively.

Plasmid pBIVC is also digested with BfrI and BgIII to remove a smaller segment of the coding region, and then blunt end-ligated to the CMV-eGFP and PGK-eGFP cassettes, as well as a DNA segment containing eGFP linked to the myeloid proliferative sarcoma virus (MND) promoter (Robbins, P. B., X. J. Yu, D. M. Skelton, K. A. Pepper, R. M. Wasserman, L. Zhu, and D. B. Kohn. 1997. J Virol. 71:9466–9474), generating plasmids pBC2CG (also named pBIVC-BBCG), pBC2PG (also named pBIVC-BBPG), and pBC2MG, respectively.

Plasmid PBBBC is digested with MunI and HpaI to remove BIV sequences between the putative RRE and the 3' LTR, then ligated to the MND-eGFP and PGK-eGFP cassettes to generate plasmids pBC3MG and pBC3PG, respectively. The CMV-eGFP cassette is also inserted into the BstEII site of plasmid pBIV to generate pBCG.

Plasmid pBC3MG is digested with BfrI and BgIII to remove the short polylinker and then (1) ligated to a ~500 bp BgIII fragment of the pBIV pol gene (containing the putative central polypurine tract) to produce plasmid pBC3MGppt; (2) ligated to a ~1 kb BfrI fragment of pBIV (containing the 5' end of the BIV gag gene) to produce plasmid pBC3MGgag; or (3) ligated to an ~800 bp fragment containing the human interferon-β scaffold attachment region (SAR; Agarwal, M., T. W. Austin, F. Morel, J. Chen, E. Böhnlein, and I. Plavec. 1998. 72:3720–3728) to produce plasmid pBC3MGsar.

Plasmid pBC3MGgag is linearized with BfrI and ligated to the SAR and cPPT fragments to produce plasmids pBC3MGgagSAR and pBC3MGgagppt, respectively.

Plasmid pBC3MGppt is linearized with BfrI and ligated to the SAR fragment to produce plasmids pBC3MGpptsar.

Plasmids pBC3MP and pBC3MPsar are generated from plasmids pBC3MG and pBC3MGsar, respectively, by replacement of the eGFP cDNA with the puromycin N-acetyltransferase cDNA (Vara, J. A., A. Portela, J. Ortin, and A. Jimenez. 1986. Nuc Acids Res. 14:4617–4624).

Plasmids pBC4MG and pBC4MGppt, in which the 3' LTR contains a large deletion in the U3 region and an insertion of the SV40 late polyadenylation signal upstream enhancer element (USE; Schek, N., C. Cooke, and J. C. Alwine. 1992. Mol Cell Biol. 12:5386–5393), are generated from plasmids pBC3MG and pBC3MGppt, respectively, as follows. First, the 5' portion of the LTR and SV40 regions is subjected to PCR amplification with primers GFP5 (5'-GAGGACG-GCAACATCCTGG-3') and BSINSV3 (5'-AGCAATAG-CATCACAAATTTCACAAATAAACA-CATATGGGAAGTCCGGG-3') while the 3' portion is subjected to PCR amplification with primers BSINSV5 (5'-GTGAAATITGTGATGCTATTGCTT-TATTTGTAATCTGTACTTCAGCTCGTGTAG-3') and BIV3 (5'-TCGCCGACATCACCGATGG-3'). Second, the two amplified products are mixed and subjected to amplification using primers GFP5 and BIV3. The final product is digested with SspBI and SphI and ligated to plasmids pBC3MG and pBC3MGppt previously digested with SspBI and SphI. The resulting plasmids, pBC4MG and pBC4MGppt, contain the 40 bp SV40 USE in place of 332 bp of the U3 region.

For the relative assessment of the BIV gene transfer system, HIV-1 and MLV gene transfer systems are used. The construction and use of such systems for this purpose involve standard techniques known to those skilled in the art.

Example 1.2

Immortalized Cells

Cells are obtained from the following sources. 293T cells are obtained from Gary Nolan (Stanford University, Palo Alto Calif.). CEMSS cells are obtained from the AIDS Reagent Program (Rockville Md.). A-10, and D-17 cells are obtained from the American Tissue Type Collection (ATCC, Manassas Va.). MN9D cells (Choi, H. K., L. A. Won, P. J. Kontur, D. N. Hammond, A. P. Fox, B. H. Wainer, P. C. Hoffmann, and A. Heller. 1991. Brain Res. 552:67–76) are obtained from Rainer Ortmann (Novartis, Basel, Switzerland). Embryonal rabbit epithelial (EREp) cells (Oberste, M. S., J. C. Williamson, J. D. Greenwood, K. Nagashima, T. D. Copeland, and M. A. Gonda. 1993. J Virol. 67:6395–6405) is obtained from the National Institutes of Health (Rockville Md.).

HUVEC (20) cells and primary rat aorta (smooth muscle) cells are obtained from Clonetics (San Diego Calif.). HUVEC cells are cultured in EBM basal media with the FGM bullet kit containing 0.1% human epidermal growth factor (hEGF), 2% fetal calf serum (FCS), 0.4% bovine brain extract w/heparin, 0.1% GA-1000 (gentamicin, amphotericin B), and 0.1% hydrocortisone.

Rat aorta cells are maintained in EBM basal media with the EGM-MV bullet kit containing 0.1% hEGF, 5% FCS, 0.4% bovine brain extract w/heparin, 0.1% GA-1000, 0.1% hydrocortisone, and cultured in Primaria tissue culture flasks (Becton Dickinson Biosciences, San Jose Calif.).

CEMSS cells are cultured in RPMI-1640 medium supplemented with 10% FCS. All other cell lines are cultured in Dulbecco's modified Eagle medium (DMEM) supplemented with 10% FCS. $1.25 \times 10^5$ HUVEC cells are suspended in 5 ml of medium and irradiated with 8000 rad from a $^{137}Cs$ source irradiator (J. L. Shepherd, San Fernando Calif.), then transferred to a 6-well dish and incubated for two days to allow for synchronization in the $G_2/M$ phase of the cell cycle.

Example 1.3

Virus Production $4–10 \times 10^6$ 293T cells are seeded into 10 cm dishes overnight and transfected the next day with 20–30 µg plasmid DNA by the calcium phosphate method (Clontech, Palo Alto Calif.). Typically, 20 µg of the vector, 10 µg of the packaging construct, and 3 µg of the VSV-G plasmid is used. In cases where the HIV-1 rev protein is required, 4 µg of plasmid pCrev is added. 24–72 hours later, the cells or the virus-containing medium is collected and analyzed in a variety of ways (see below). To assess the efficiency of transfection, a portion of the cells are analyzed for eGFP expression by flow cytometry, using a FACScan (Becton Dickinson Biosciences, San Jose Calif.). To measure the amount of virus shed into the medium, the medium is cleared of cellular debris by low-speed centrifugation, then 10 µl is lysed and analyzed for RT activity using a commercial kit (Roche Molecular Biochemicals, Indianapolis, Ind.).

Example 1.4

Analysis of RNA Levels: Northern Assay

Transfected cells are lysed and cytoplasmic RNA is prepared using a commercial kit (Qiagen, Valencia Calif.). In addition, virus-containing medium is collected, subjected to low-speed centrifugation to remove cellular debris, and then subjected to high-speed centrifugation (50,000×g for 90 minutes at 4° C.) to collect the virus particles. The viral pellet is lysed and the viral RNA is prepared using a commercial kit (Qiagen, Valencia Calif.). A fixed amount of cytoplasmic RNA (10 µg) or viral RNA (one third of the RNA preparation, not quantitated) is subjected to 1% agarose gel electrophoresis and transferred to a nylon filter (Bio-Rad, Hercules Calif.). The filter is exposed to $40 \times 10^6$ cpm of a DNA fragment random-primed with $^{32}P$-dCTP using a commercial kit (Ambion, Austin Tex.), then washed and analyzed for bound probe with a phosphoimager (Molecular Dynamics, Sunnyvale Calif.). The probes include a BIV gag fragment, an HIV-1 gag fragment (both ~1 kb in size), a ~330 bp BIV U3 fragment, and an ~800 bp eGFP fragment.

Example 1.5

Analysis of Protein Levels: Western Assay

Transfected cells are lysed on ice for 1 hour in a buffer containing 1% NP-40, 150 mM NaCl, 10 mM Tris-Cl pH 7.4, 1 mM EDTA, and Pefabloc protease inhibitor (Roche Molecular Biochemicals, Indianapolis, Ind.). The lysate is subjected to centrifugation at 8,000×g for 20 minutes at 4° C. to remove precipitated proteins and other debris. Alternatively, virus-containing medium is collected, subjected to brief centrifugation to remove cellular debris, and then subjected to high-speed centrifugation (50,000×g 90 minutes at 4° C.) to collect the virus particles. The viral pellet is lysed directly in SDS-PAGE sample buffer (Novex, San Diego Calif.). A fixed amount of cell or viral lysate is subjected to acrylamide gel electrophoresis and transferred to a nitrocellulose filter. The filter is exposed to rabbit serum specific for BIV Gag protein (obtained from the National Institutes of Health), then to horseradish peroxidase (HRP)-conjugated goat anti-rabbit Ig antibody (Zymed, South San Francisco Calif.), then to the HRP substrate OPD (Sigma, St.

Louis Mo.). Prestained molecular weight standards (Bio-Rad, Hercules Calif.) are used to determine the approximate molecular weight of the BIV Gag bands. For the HIV western blot, the filter is exposed to biotinylated anti-HIV Gag antibody (Beckman Coulter, Fullteron Calif.) and then to steptavidin-conjugated HRP (Beckman Coulter, Fullteron Calif.) before the OPD reaction. For the HA western blot, the filter is exposed to a biotinylated anti-HA antibody (Roche Molecular Biochemicals, Indianapolis, Ind.), then to the steptavidin-conjugated HRP before the OPD reaction. For the VSV-G western blot, the filter is exposed to mouse anti-VSV-G monoclonal antibody (Sigma, St. Louis Mo.) and then to an HRP-conjugated goat anti-mouse Ig antibody (Zymed, South San Francisco Calif.) before the OPD reaction.

Example 1.6

Analysis of Transduction

To transduce cells, the virus-containing medium is subjected to brief centrifugation to remove cellular debris, then 1 ml is added to fresh cells in polypropylene tubes ($5 \times 10^5$ CEMSS cells) or in 6-well dishes ($3–6 \times 10^5$ adherent cells seeded per well the previous day). Protamine sulfate (Sigma, St. Louis Mo.) is added to the wells at a final concentration of 8 μg/ml and the tubes/dishes are subjected to centrifugation ("spinoculation") at 3000 rpm for 2–3 hours at 32–37° C. In later experiments, the tubes/wells are also supplemented with 10 mM HEPES buffer prior to spinoculation to prevent the pH of the medium from rising while the cells are in the centrifuge. After spinoculation, the tubes and dishes are processed in different ways: supernatant is aspirated from the tubes, the CEMSS cells are suspended in fresh medium and transferred to 6-well dishes. In contrast, the spinoculated dishes are placed back into the incubator for 30–60 minutes, then the medium is removed and fresh medium is added to the wells. 2–3 days post-spinoculation, a portion of the cells are removed from the plate and analyzed for eGFP expression by flow cytometry, using a FACScan (Becton Dickinson Biosciences, San Jose Calif.). For virus preparations containing the vectors pBC3MP and pBC3MPsar, 293T cells are subjected to spinoculation with serial dilutions of the virus-containing medium, and fresh medium supplemented with 5 μg/ml puromycin is added to the cells 24 hours post-spinoculation. 7–10 days later, colonies are counted by direct visualization.

Example 1.7

Infection of Primary T Cells

Human peripheral blood mononuclear cells (PBMC) are isolated from adult peripheral whole blood by Ficoll density gradient centrifugation, rinsed in phosphate-buffered saline (PBS), and suspended in RPMI-1640 medium supplemented with 10% FCS. A portion of the PBMC are activated by adding IL2 (Peprotech, Rocky Hill N.J.) to the medium at a final concentration of 200 U/ml and culturing the cells for 3 days in 12-well dishes ($3 \times 10^6$ cells per were-coated as follows: the dishes are incubated with 1 μg/ml goat anti-mouse Ig Fc (Pierce, Rockford Ill.) for 3 hours, rinsed with PBS, incubated with a mixture of 1 ug/ml anti-CD3 (OKT3) and 10 ng/ml anti-CD28 (BD Pharmingen, San Diego Calif.) monoclonal antibodies for 1 hour, and rinsed with medium. $5 \times 10^5$ activated or unstimulated PBMC are spinoculated with viral supernatant in polypropylene tubes similar to CEMSS cells (see above); after spinoculation, the cells are rinsed and suspended in medium containing IL2 and cultured in 24-well dishes pre-coated with the anti-CD3 and anti-CD28 mAbs. Four days and two weeks later, a portion of the cells are removed from the well and analyzed for eGFP expression by flow cytometry, using a FACScan (Becton Dickinson Biosciences, San Jose Calif.). T cells are identified by light scatter properties and by expression of CD4 and CD8, using APC-conjugated anti-CD4 and PerCP-conjugated anti-CD8 mAbs (Becton Dickinson Biosciences, San Jose Calif.).

Example 1.8

Infection of Hematopoietic Stem Cells (HSCs)

Human CD34$^+$ cells are isolated from G-CSF-mobilized peripheral whole blood from normal donors using Isolex 300SA (Baxter, Ill.). The cells (80–90% pure CD34$^+$) are aliquoted ($1 \times 10^7$) and frozen in medium consisting of 45% Iscove's modified Eagle medium (IMDM), 45% FCS and 10% DMSO. Prior to transduction, the frozen cells are first thawed in buffer containing 2% FCS, 1% HEPES, and 10 U/ml Heparin. After thawing, the cells ($5 \times 10^5$) are either spinoculated (see above) with viral supernatant in the absence of cytokines or cultured for 48 hours in cytokine-containing medium (X-vivo 15 medium (BioWhittaker, Walkersville Md.), thrombopoietin (tpo) mimetic (50 ng/ml; Novartis, Basel, Switzerland), flt3 ligand (100 ng/ml), and c-kit ligand (100 ng/ml; both from Systemix, Palo Alto Calif.)) and then spinoculated with viral supernatant. After infection, the cells are cultured in cytokine-containing media. Three days or two weeks later, a portion of the cells is stained with APC-conjugated anti-CD34 antibody (Becton Dickinson Biosciences, San Jose Calif.) and analyzed for eGFP on the CD34$^+$ cells on a FACScan (Becton Dickinson Biosciences, San Jose Calif.).

Example 2

Transduction of Human Cells with BIV

The wild-type BIV genome is modified by insertion of the enhanced green fluorescent protein (eGFP) marker gene, producing construct BCG (for details of plasmid construction see example 1). The eGFP gene is inserted into an interior position within the viral envelope gene so as not to affect viral rev or tat expression or rev-response element (RRE) function. The human kidney carcinoma cell line 293T is cotransfected with construct BCG and a plasmid encoding the vesicular stomatitis virus glycoprotein (VSV-G); two days later, the virus-containing medium is collected and exposed to fresh 293T cells. In addition, the medium is added to the embryonal rabbit epithelial cell line EREp, which supports wild-type BIV replication (Oberste, M. S., J. C. Williamson, J. D. Greenwood, K. Nagashima, T. D. Copeland, and M. A. Gonda. 1993. J Virol. 67:6395–6405.). Three days later, the exposed cells are assayed for eGFP expression by flow cytometry. A subset of the 293T cells (approximately 5%) express eGFP, indicating that BIV can carry out all of the functions (including reverse transcription and integration) required for transduction of human cells. Similar transduction efficiencies are noted for the EREP cell line.

Example 3

BIV Packaging Constructs

Figure 2:
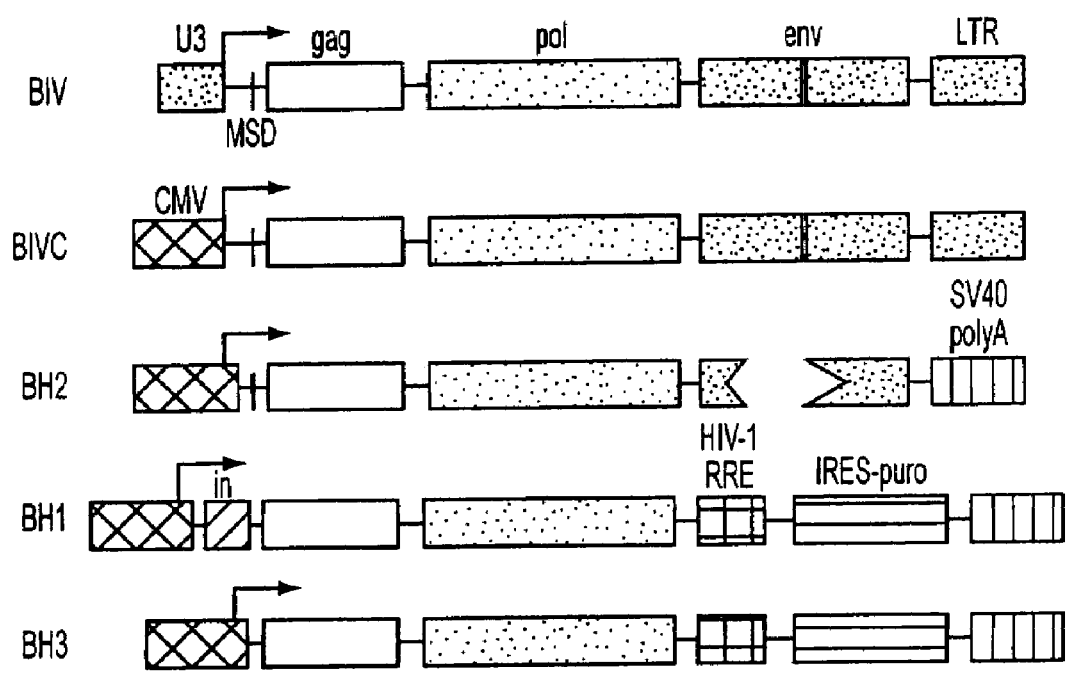
FIG. 2: BIV packaging constructs: Wild-type BIV, CMV-driven BIV, and three packaging constructs (BH1–3) are depicted for their gag, pol, and env genes; accessory genes are not shown. Also depicted are the viral major splice donor (MSD), a small chimeric intron (in), the HIV-1 rev-response element (RRE), the puromycin N-acetyltransferase cDNA linked to an internal ribosome entry site from encephalomyocarditis virus (IRES-puro), and the SV40 late polyadenylation signal (SV40 polyA).

Packaging constructs containing the viral genes are generated as described in example 1 (FIG. 2) and assayed for gag mRNA expression and virus production (Table 1) in the transient expression system.

TABLE 1

Virus production by the BIV constructs[a]

| Construct | expt#1 | Expt#2 | expt#3 | expt#4 | expt#5 | expt#6 | expt#7 |
|---|---|---|---|---|---|---|---|
| HIV | 132 | 121 | 115 | 123 | 121 | | |
| BIV | 0 | 1 | 4 | | | | |
| BIVC | 1 | 5 | | | | | |
| BH2 | 39 | 137 | | 79 | 276 | 464 | 624 |
| BH1 | | 0 | | | | | 14 |
| BH3 | | 0 | | | | 0 | |

[a]Virus-containing media is collected from 293T cells transfected with the indicated Construct and analyzed by RT assay. Seven transfections are performed. Values are given in pg of RT protein per ml media.

One construct, BIVC, is identical to wild-type BIV except for a precise replacement of the 5' LTR U3 region with the human cytomegalovirus (CMV) immediate-early promoter. The junction between the 2 segments is located at the identical TATA boxes to maximize the chances that the viral RNA would contain the proper 5' end for infection of target cells. The three other BIV packaging constructs contain the CMV promoter linked to the BIV leader near of the gag gene, deleting the 5' LTR and primer binding site and—in the case of constructs BH1 and BH3—the major splice donor. Construct BH1 contains a small chimeric intron inserted between the CMV and BIV segments. Downstream of the pol gene, construct BH2 contains all viral coding sequences except for a deletion (approximately 1 kb) of the interior of env (not predicted to affect tat and rev expression or RRE function), while constructs BH1 and BH3 contain BIV sequences terminating approximately 250 bp downstream of the pol gene. Since BH1 and BH3 lack the rev gene and the RRE, the HIV-1 RRE is inserted downstream of the BIV sequences and HIV-1 rev protein is provided in trans when the constructs are characterized. In addition, these two constructs contain the puromycin N-acetyltransferase cDNA (Vara, J. A., A. Portela, J. Ortin, and A. Jimenez. 1986 Nuc Acids Res. 14:4617–4624) coupled to an internal ribosome entry site (IRES) from the encephalomyocarditis virus (ECMV; Jang, S. K., M. V. Davies, R. J. Kaufman, and E. Wimmer. J Virol. 63:1651–1660), for selecting cell lines stably producing the packaging construct.

Northern analysis of transfected cell cytoplasmic RNA indicates that construct BIVC produced higher steady-state levels of gag mRNA (816 cpm) than did wild-type BIV (249 cpm) or construct BCG (113 cpm), suggesting that the CMV promoter is more active than the BIV LTR in 293T cells. Packaging constructs BH1 (70 cpm) and BH3 (39 cpm) express low levels of gag mRNA, but BH2 (861 cpm) express high levels comparable to construct BIVC. For comparison, a CMV-driven HIV-1-derived packaging construct is observed to express even higher levels of gag mRNA (1120 cpm).

Reverse transcriptase (RT) assay (Table 1) and western blot analysis of virus collected from the transfected cells indicate that BIVC produces more virus particles than did wild-type BIV, BH1 and BH3, but much less than BH2 or the HIV-1 packaging construct. The low amount of BIVC virus may have been due to toxicity in the transfected cells resulting from BIVC's high-level expression of the wild-type BIV envelope protein, as cytopathic effects and small syncytia are observed in the culture. Western blot analysis indicates that both the BIVC and BH2 virus preparations have undergone maturation, i.e. the Gag polyprotein is almost entirely cleaved.

The RT assay indicates that the amount of virus produced by BH2 is similar to that produced by the HIV-1 packaging construct. To verify that the amounts of virus are similar, these two packaging constructs are modified by insertion of two consecutive hemagglutinin (HA) tags immediately upstream of the gag stop codon. The HA-tagged constructs, which are further deleted for most of the pol gene to block Gag polyprotein cleavage, are introduced into 293T cells alongside the parental constructs. The modified virus is collected two days later and compared to the parental virus by western blot assay using antibodies specific for Gag protein: both modified constructs produce amounts of virus similar to the parental constructs. The modified viruses are then normalized by RT assay of the parental constructs (649 pg for HIV-1, 205 pg for BH2) and analyzed for HA tag content by western blot assay. The amounts of HA-tagged HIV-1 Gag polyprotein and HA-tagged BIV Gag polyprotein are similar, corroborating the RT assay: the BH2 packaging construct produce levels of virus roughly similar to the HIV-1 packaging construct.

Western blot analysis is also performed on the BH2 and HIV-1 virus preparations to assess the efficiency of VSV-G incorporation. Virus is collected from 293T cells transfected with each packaging construct and the VSV-G construct, then normalized by RT assay and subjected to western blot analysis using a monoclonal antibody specific for VSV-G. The amount of VSV-G detected in the BH2 and HIV-1 samples is similar, indicating that BIV incorporates VSV-G as efficiently as HIV-1.

Example 4

BIV Vectors

BIV-derived vectors are generated, as described in detail in example 1, containing the eGFP marker gene and all viral elements required in cis for transfer into target cells.

First, the two vectors (BCCG and BCPG) containing the full leader, but no gag sequences, and minimal env sequences (i.e. no RRE) are compared to the analogous vectors (BC2CG and BC2PG) containing approximately 500 bp of gag sequences and 1.2 kb of env sequences (including the putative RRE). The latter vectors are generated because previous studies with other retroviruses have indicated that the 5' end of the gag gene increases the extent of vector RNA encapsidation in the virus particles, either by containing packaging elements or by stabilizing packaging elements further upstream (Bender, M. A., T. D. Palmer, R. E. Gelinas, and A. D. Miller. 1987. J Virol. 61:1639–1646, Buchschacher, G. L., and A. T. Panganiban. 1992. J Virol. 66:2731–2739; Parolin, C. P., T. Dorfman, G. Palu, H. Gottlinger, and J. Sodroski. 1994. J Virol. 68:3888–3895). In addition, studies with HIV-1 have indicated that the gag gene contains sequences which block RNA export from the nucleus, and that the RRE removes this block in the presence of the rev protein (Malim, M. H., J. Hauber, S. Y. Le, J. V. Maizel, and B. R. Cullen. 1989. Nature. 338:254–257; Schwartz, S., B. K. Felber, and G. N. Pavlakis. 1992. J Virol. 66:150–159). The two vectors containing the PGK internal promoter are analyzed for transduction in 293T cells, using the BH2 packaging construct pseudotyped with VSV-G: BC2PG transduces 5% of the cells, while BCPG transduced none of the cells (FIG. 3, Exp.#1). All four vectors are then assessed for cytoplasmic RNA expression in transfected 293T cells and in collected BH2 virions by northern blot analysis. Each of the vectors produces high levels of full-length vector RNA in the transfected cell cytoplasm, but only the BC2CG and BC2PG full-length RNAs are encapsidated efficiently by the BH2 virions. Therefore, the 5' end of the BIV gag gene is likely to contain sequences directly or indirectly required for viral RNA encapsidation. Interestingly, without those sequences on the BCPG and BCCG full-length RNAs, the internally-initiated mRNAs are encapsidated, suggesting that other packaging elements reside in the 3' portion of the BIV genome (Berkowitz, R. D., J. Fisher, and S. P. Goff. 1996. Current Topics in Microbiology and Immunology. 214:177–218).

Next, the PGK promoter is compared to the MND promoter in two contexts, i.e. with the promoter-eGFP cassette upstream (BC2PG and BC2MG) or downstream (BC3PG and BC3MG) of the putative BIV RRE. In 293T cells, the latter context produces slightly higher transduction efficiencies than the former (14% vs. 6% for the PGK vectors and 35% vs. 29% for the MND vectors), and in both contexts the MND promoter performs better than the PGK promoter (FIG. 3, Exp.#2). However, all vectors transduces substantially fewer cells than did an HIV-1 virus containing an analogous PGK-eGFP vector (75% transduction).

Virus containing the optimal vector, BC3MG, is then produced and analyzed for its ability to be concentrated by centrifugation, for its ability to transduce a lymphoid cell line, and for the change in the frequency of eGFP expression over two weeks post-infection. A portion of the virions are collected by centrifugation, suspended in a volume 100-fold lower than the original volume, and then diluted either 10-fold or 100-fold. Although the 1× virus exhibits low transduction efficiencies, the T lymphoid cell line CEMSS is transduced more efficiently (12%) than the 293T cells (5%). In addition, the 10× virus transduces a 10-fold higher percentage of 293T cells, and a 4.5-fold higher percentage of CEM cells. Moreover, the percentage of eGFP$^+$ cells decreases approximately 5-fold over two weeks in the 293T line, and to a much lesser extent in the CEMSS line. Subsequent infections with new, unconcentrated virus preparations indicates that the fold-reduction in the percentage of eGFP$^+$ 293T cells over time correlates inversely with the initial percentage of eGFP$^+$ cells. For example, 293T cells which are 73% eGFP$^+$ 2 days post-infection are found to be 43% eGFP$^+$ 2 weeks post-infection and 28% eGFP$^+$ 4 weeks post-infection.

The higher transduction efficiencies exhibited by the BC3 vectors relative to the BC2 vectors may be due to a increased stability of the packaging signal, due to its positioning farther away from non-viral sequences, i.e. the internal promoter (Kaye, J. F., J. H. Richardson, and A. M. L. Lever. 1995. J Virol. 69:6588–6592). Additional viral segments are therefore inserted immediately downstream of the gag region in vector BC3MG, including an approximately 500 bp segment of the pol gene, containing polypurine tracts that may function in an analogous manner to the central polypurine tract (cPPT) region of HIV-1 (Chameau, P., M. Alizon, and F. Clavel. 1992. J Virol. 66:2814–2820, Chameau, P., Mirambeau., R. G, P., S. Paulous, H. Buc, and F. Clavel. 1994. J Mol Biol. 241:651–662). In addition, the 3' portion (approximately 1 kb) of the gag gene is inserted: this vector (BC3MGgag) contains the entire gag gene except for approximately 200 bp in the capsid domain. The two new vectors are found to transduce slightly higher frequencies of 293T cells (70% and 73%) than the parental vector BC3MG (55%) when used with BH2 and VSV-G (FIG. 3, Exp.#3). For comparison, an HIV-1 virus containing an MND-eGFP vector transduces 100% of the cells.

The β-interferon scaffold attachment region (SAR), which has been shown to potentiate vector expression from integrated proviral DNA (Agarwal, M., T. W. Austin, F. Morel, J. Chen, E. Böhnlein, and I. Plavec. 1998. Journal of Virology. 72:3720–3728), is also inserted immediately downstream of the packaging signal. This vector, BC3MGsar, transduces a slightly higher frequency of 293T cells than did the BC3MGppt vector (71% vs. 60%; FIG. 3, Exp.#4). In addition, vectors containing pairwise combinations of the SAR segment, the 3' gag segment, and the cPPT segment are generated; however, none of these vectors exhibit higher transduction efficiencies than the vectors containing the individual segments alone (FIG. 3, Exp.#4).

The BC3MG and BC3MGppt vectors are then compared to their SIN counterparts, BC4MG and BC4MGppt. These SIN vectors are deleted in the interior 322 bp of the U3 region of the 3' LTR, retaining 55 bp at the 5' end and 7 bp at the 3' end; as a result, the TATA box and most of the promoter elements are removed. Vectors deleted in this area are termed "self-inactivating", or SIN, because the integrated vector in the target cell possesses a 5' LTR incapable of directing transcription (Miyoshi, H., U. Blomer, M. Takahashi, F. H. Gage, and I. M. Verma. 1998. J Virol. 72:8150–8157, Zufferey, R., T. Dull, R. J. Mandel, A. Bukovsky, D. Quiroz, L. Naldini, and D. Trono. 1998. J Virol. 72:9873–9880). This effect not only increases the safety of the vector, but in cases where transcription from the 5' LTR interferes with transcription from the vector's internal promoter, the SIN deletion may also increase transgene expression in the transduced cell. It has also previously been reported that read-through transcription occurs from an integrated HIV-1 provirus (Dron, M., L. Hameau, L. Benboudjema, J. Guymarho, C. Cajean-Feroldi, C. Rizza PGodard, C. Jasmin, M. G. Tovey, and M. C. Lang. 1999. Arch Virol. 144:19–28), suggesting that HIV-1 transcripts do not always terminate at the 3' LTR. Since this phenomenon might also occur in the BIV vectors, and might decrease the titer of the gene transfer system (Carswell, S., and J. C. Alwine. 1989. Mol Cell Biol. 9:4248–4258), the SV40 late polyadenylation signal upstream enhancer element (USE; Schek, N., C. Cooke, and J. C. Alwine. 1992. Mol Cell Biol. 12:5386–5393) is inserted into the gap created by the SIN deletion. The two new vectors (BC4MG and BC4MGppt) are analyzed for transduction efficiency with packaging construct BH2 and VSV-G: BC4MG transduces 68% of the 293T cells, while BC4MGppt transduces 90% (FIG. 3, Exp.#5). However, since the parental, non-SIN vectors exhibit similar transduction efficiencies (68% and 84%, respectively), the SIN deletion and SV40 USE insertion do not substantially increase the titer of the BIV gene transfer system.

To determine the titer of the BIV viruses with precision, the eGFP cDNA is removed from vectors BC3MG and BC3MGppt and replaced with the puromycin N-acetyltransferase cDNA (Vara, J. A., A. Portela, J. Ortin, and A. Jimenez. 1986. Nuc Acids Res. 14:4617–4624), generating vectors BC3MP and BC3MPppt. The same is done for the HIV-1 vector containing the MND-eGFP cassette. The three viruses are prepared in 293T cells and serial dilutions are exposed to fresh 293T cells; after two days, the cells are treated with puromycin to kill the non-transduced cells.

After a week in culture, the number of colonies growing in the dishes are counted and used to calculate the titer of the original viruses. The HIV virus titer is $1.2 \times 10^7$ per ml, the BC3MP virus titer is $3 \times 10^5$ per ml and the BC3MPppt titer is $4.5 \times 10^5$ per ml, nearly 30-fold lower than the HIV virus titer.

Example 5

Transduction of Other Cell Lines and Non-Dividing Cells

Concentrated BIV virus, prepared in 293T cells using packaging construct BH2, vector BC3MG, and VSV-G, is used to transduce a panel of cell lines: D-17, a dog osteosarcoma line; A-10, a rat smooth muscle cell line; HUVEC, a human endothelial cell line; and MN9D, a mouse neuronal cell line. In each of these cell lines, the BIV virus transduced a large percentage (63–88%) of the cells, even two weeks post-infection. In addition, primary rat endothelial cells are transduced by the BIV virus, albeit not as efficiently as the immortalized lines (22%).

To assess the ability of the BIV virus to transduce non-dividing cells, the concentrated BIV virus (10×) is assayed for transduction of irradiated HUVEC cells and resting human peripheral blood lymphocytes (PBLs). The HUVEC line is irradiated two days before exposure to the BIV virus, to synchronize the cells at the $G_2/M$ phase of the cell cycle. As expected, a murine leukemia virus (MLV) virus preparation is observed to readily transduce the untreated cells but not the irradiated cells. In contrast, both the BIV and HIV-1 viruses transduce the untreated and irradiated cells with similar efficiencies, indicating that each lentivirus is able to transduce the non-dividing cells efficiently.

In unstimulated human PBLs, the BIV virus exhibits transduction efficiencies similar to the HIV-1 virus when the cells are assayed four days after infection, although most of the BIV-transduced cells expresses very low levels of eGFP. Two weeks post-infection, however, these dim cells are nearly absent from the population. As a result, the percentage of transduced cells is low: 1% for the 10× virus and 6% for the 40× virus. However, the virus also exhibits low transduction efficiencies in pre-activated (i.e. proliferating) PBLs, as the 10× virus transduced only 5% of the cells. In contrast, 10×HIV-1 virus transduced 81% of the pre-activated cells and 44% of the unstimulated cells, while 10×MLV virus transduced 43% of the pre-activated cells but only 1% of the unstimulated cells.

Finally, the concentrated BIV virus is used to transduce unstimulated mobilized peripheral CD34+ hematopoietic stem cells (HSCs), most of which are quiescent (Knaan-Shanzer, F., D. Valerio, and V. W. van Beusechem. 1996. Hum Gene Ther. 3:323–333 Uchida, N., D. He, A. Friera, M. Reitsma, D. Sasaki, B. Chen, and A. Tsukamoto. 1997. Blood. 89:465–472). The 10×BIV preparation transduces 19% of the HSCs three days post-infection, while the 40×BIV virus transduced 31% of the cells. Interestingly, almost all of the cells transduced with the 10×BIV virus express high levels of eGFP, and these cells do not disappear when the cells are analyzed 11 days later. The cells infected with the 40×BIV virus contain two eGFP+ populations: one (18% of the cells) which expressed very low levels of eGFP and one (13% of the cells) which expressed higher levels of eGFP. Both populations exhibited 6-fold reductions in frequency over the next 11 days.

Example 6

BIV Based Gene Transfer System

Example 6.1

Abbreviations

HIV: Human Immunodeficency Virus
BIV: Bovine Immunodeficiency Virus
VSV-G: Vesicular Stomatitis Virus Envelope Glycoprotein G
MLV: Murine Leukemia Virus
MV: Adeno-Associated Virus
IU: Infectious Unit
HSkMC: Human Primary Skeletal Muscle Cells Example 6.2

Introduction

Various viral vectors have been explored as vehicles to deliver therapeutic genes for human gene therapy. Murine leukemia virus (MLV), adenovirus, and adeno associated virus (MV) based vectors have been widely used for such purposes. However, all these vector systems have their advantages as well as disadvantages. MLV based vectors have been proven to be safe for human gene therapy, yet they suffer from an inability to transduce non-dividing cells, which are often the therapeutic targets in vivo. Human adenovirus based vector are capable of efficiently transducing a variety of non-dividing target cells. However, a strong host immune reaction and transient gene expression has limited the applications of the most commonly used avenovirus vectors. The low coding capacity of MV based vectors decreases the utility of these vectors.

Recently, lentiviruses based vector systems have been extensively studied for their potential use as a gene delivery system. Lentiviral vectors can efficiently transduce both dividing and non-dividing cells, and they stably integrate into host chromosomes, resulting in long-term gene expression. The vector system also offers wide tropism due to its ability to pseudotype with heterologous viral envelopes. In addition, lentiviral vectors potentially raise no concern over the issue of host immune reaction, owing to the fact the only the transgene is expressed in the target cells. In vitro, it has been shown that Human immunodeficiency virus (HIV) based VSV-G pseudotyped lentiviral vectors transduce a variety of non-dividing cells, e.g. microphages, neurons, hepatic cells, photoreceptor cells, and hematopoetic stem cells. In vivo, lentiviral vectors have been shown to transduce rat neurons, resulting in long term transgene expression.

To circumvent the safety concerns related to HIV based lentiviral vectors, we have developed a Bovine Immunodeficiency Virus (BIV) based lentiviral vector system. BIV is not a human pathogen and does not cause obvious disease in its natural host, cattle. We show here that 1) our BIV based lentiviral vector has a titer of $1.2 \times 10^6$ i.u./ml, which is comparable with HIV based systems; 2) the BIV based vectors can be concentrated more than 150 fold with a one ultracentrifugation step; and 3) the BIV based vectors efficiently transduce both dividing and non-dividing human primary skeletal muscle cells.

Example 6.3

Methods

Cells. Human primary skeletal muscle cells (hSkMC) were purchased from Clonetics (Clonetics, Walkersville, Md.) and maintained and cultured according to the manufacture's instructions. Human embryonic kidney 293T cells were cultured in Dulbecco's Modified Eagle's medium (DMEM, BioWhittaker, Walkersville, Md.) containing 10% fetal bovine serum (complete DMEM medium) (FBS, Hyclone Labs, Logan, Utah).

BIV based gene transfer system. The BIV based gene transfer system contains three plasmid constructs: a BIV packaging construct to provide the helper function; a BIV lentiviral vector backbone encoding a marker gene, such as eGFP, or a drug resistant gene, such as puromycin resistant gene; and an expression construct encoding the VSV-G expression gene. The BIV lentiviral vector backbone and the VSV-G expression construct are essentially the same as described above. However, the BIV packaging construct BH2 was modified. Specifically, a 15 bp putative packaging sequence from the major splicing donor site (MSD) to BIV gag start codon was deleted, generating BH2Δψ. In order to delete the putative packaging sequence, the region between MSD to gag start codon was subjected to PCR amplification with two primers PackageDel 5 (5'-CGACCCGGGCGGC-CGCTTCG-3') and PackageDel 3 (5'-CTACTCACCTGTC-CGGAGTC-3'). The amplified PCR product was digested with SmaI and ligated to BH2 plasmid previously digested with SmaI giving rise to BH2Δψ.

Preparation of BIV lentiviral vector. To generate BIV lentiviral vector, 85% confluent. 293T cells in a 10 cm dish were transfected with 15 μg packaging plasmid (BH2Δψ), 15 μg vector plasmid (BIVMNDeGFP or BIVMNDPuro), and 4.5 μg VSV-G expressing plasmid (pCMV.VSV-G) using casium phosphate based transfection system. Vector supernatant was harvested 48 hr post-transfection and filtered through a 0.45 μM filter. The vector was then aliquoted and stored at −80° C. until use. To concentrate BIV lentiviral vector, the vector supernatant harvested was subjected to ultracentrifugation for 90 minutes at 100,000×g at 4° C. The pelleted vector was resuspended in a small volume of DMEM medium and aliquots were stored at −80° C. until use.

Transduction. Target cells were transduced with lentiviral vector for four hours in the presence of 8 μg/ml protamine sulfate (Sigma, St. Luis, Mo.). The cells were then washed with cell culture medium twice and continuously cultured for additional 48 hours. The transduced cells were then analyzed for eGFP expression with FACScan.

Titration of BIV lentiviral vector. To titer BIV based lentiviral vector, $5 \times 10^4$ 293T cells were plated in each well of a six-well plate on day one. On day two, a lentiviral vector (5 μl of nonconcentrated supplemented with 2 ml of complete DMEM medium) encoding puromycin resistant gene was used to transduce the cells in the presence of 8 μg/ml protamine sulfate. On Day three, the transduced cells were trypsinized and 5% of the transduced cells from each well were plated in a 6 cm dish with 5 ml of complete DMEM medium in the presence of 5 μg/ml of Puromycin (Sigma, St. Luis, Mo.). Three days later, the medium was changed with fresh cell culture medium with puromycin. Day seven post-transduction, the cell culture medium was aspirated and the puromycin resistant clones were stained with coomassie blue and counted.

Reverse transcriptase assay. Taking advantage of the fact that BIV RT cross-reacts with HIV RT, we quantitated BIV RT with an HIV RT assay kit purchased from Roche.

BrdU incorporation. To determine whether the cells were actively dividing when the cells were transduced, the cells were labeled with BrdU (BrdU labeling kit, purchased from Phamingen, San Diego, Calif.) according to the manufacture's instruction.

Example 6.4

Results

Figure 4:
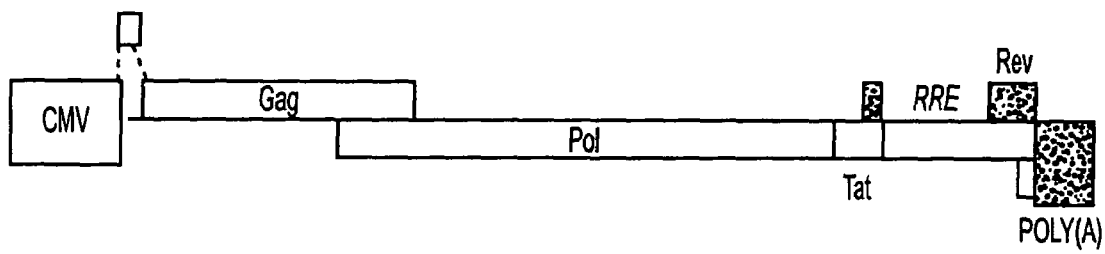
FIG. 4. Schematic illustration of the BIV based gene transfer system consists of packaging construct, vector backbone, and VSV-G expression construct. CMV: CMV early promoter; cPPT: central polypurine tract; RRE: Rev response element; MND: MND LTR; SIN: Self inactivated; SV40USE: SV40 upstream polyadenylation enhance element.
Figure 4:
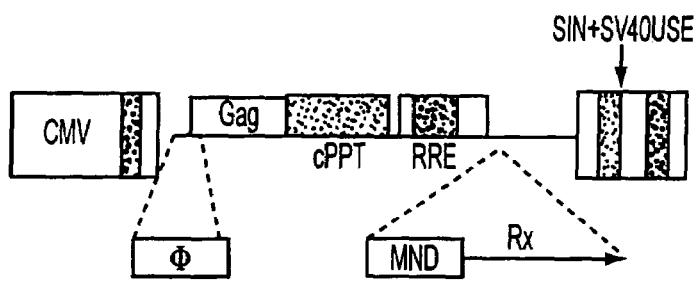
Figure 4:

BIV based gene transfer system. The BIV based gene transfer system consists of a BIV packaging construct, BIV vector construct, and VSV-G expression construct (FIG. 4). To generate BIV lentiviral vector, the three constructs were co-transfected into 293T cells, and the viral vector supernatant was harvested 48 hour post transfection as described in Methods.

Titer of a BIV based lentiviral vector. In order to determine the approximate titer of BIV based lentiviral vector, plasmid BH2Δψ (15 μg), BMNDpuro (a BIV lentiviral vector backbone with MND LTR promoting puromycin resistant gene) (15 μg), and pCMV.VSV-G (4.5 μg) were cotransfected into 293T cells as described in Methods. As a control, BMNDpuro was replaced with BMNDeGFP (puromycin resistant coding gene in BMNDpuro was replaced with eGFP coding gene). The resulting BIV lentiviral vectors, encoding puromycin resistant gene or eGFP, were used to transduce 293T cells. After puromycin selection, the puromycin resistant clones were counted. The vector achieved approximately $1.2 \times 10^6$ puromycin resistant clones per ml, suggesting that the BIV lentiviral vector has a titer of approximately $1.2 \times 10^6$ i.u./ml. These clones were BIVMNDpuro specific as no puromycin resistant clones were found in the cells transduced with BIVMNDeGFP.

Concentration of BIV based lentiviral vector. In order to obtain a higher titer of BIV lentiviral vector, the vector supernatant was subjected to untracentrifugation. The vector's RT activity before and after concentration was measured and compared. As shown in Table 2, from three independent vector preparations, the RT activity increased by more than 150 fold.

TABLE 2

Concentration of BIV based lentiviral vectors. Three independent BIV lentiviral vector preparations were subjected to utracentrifugation. The Reverse Transcriptase (RT) activity was measured before and after concentration. After one round of untracentrifugation, the RT activities were increased by more than 150 fold for all three independent preparations with two different BIV vectors.

| | Reverse Transcriptase Activity | | |
|---|---|---|---|
| BIV Vector | Before Concentration (ng/ml) | Post Concentration (ng/ml) | Fold of Concentration |
| BIVMNDLuc | 22 | 4100 | 186 |
| BIVMNDeGFP | 47 | 8130 | 172 |
| BIVMNDeGFP | 61 | 10200 | 167 |

Transduction of dividing human primary skeletal muscle cells by a BIV lentiviral vector. $1 \times 10^5$ human primary skeletal muscle cells were plated in each well of a six-well plate. The next day, the cells were labeled with BrdU or transduced with BMNDeGFP (120 ng RT equivalent for each well) for 3 hours in the presence of protamine sulfate as described in Methods. The transduced cells were analyzed for BrdU incorporation 16 hours post-transduction or eGFP expression 48 hours post-transduction with a flow cytometer. The hSkSMC were transduced efficiently with BIV based lentiviral vector BMNDeGFP. More than 56% of the cells were positive for eGFP expression with a relative mean eGFP intensity of more than 2300, suggesting that BIV based lentiviral vector can efficiently transduce human primary skeletal muscle cells. These cells were actively dividing at the time the cells were transduced as indicated by active BrdU incorporation by the cells.

Transduction of non-dividing human primary skeletal muscle cells by a BIV lentiviral vector. To stop the cell cycling, hSkSMC were irradiated with gamma-irradiator at 3500 rads. $2\times10^5$ irradiated cells were plated in each well of a six-well plate. The next day, the cells were labeled with BrdU or transduced with BMNDeGFP (120 ng RT equivalent for each well) for 3 hours in the presence of protamine sulfate as described in Methods. The transduced cells were analyzed for BrdU incorporation 16 hours post-transduction or eGFP expression 48 hours post-transduction with a flow cytometer. The non-dividing hSkSMC were transduced efficiently with BIV based lentiviral vector BMNDeGFP. More than 59% of the cells were positive for eGFP expression with a relative mean eGFP intensity more than 1500, suggesting that BIV based lentiviral vector can efficiently transduce non-dividing human primary skeletal muscle cells. These cells were confirmed to be non-dividing at the time the cells were transduced as indicated by a lack of BrdU incorporation.

Example 6.5

Discussion

Lentivirus based vectors have emerged as a promising gene transfer technology for human gene therapy. Lentiviral vectors are able to efficiently transduce both dividing and non-dividing cells both in vitro and in vivo, resulting in long-term transgene expression. Sustained long-term therapeutic gene expression is required for certain applications where life long gene expression is needed to achieve therapeutic effect. These include diseases such as neuronal diseases, metabolic disorders, and some ocular diseases. The majority of these diseases have no effective therapies.

Although a variety of lentivirus based gene transfer systems have been documented, the most efficient system has been HIV based. Safety is of paramount importance for viral vector based gene therapy. To circumvent the potential safety concerns related to HIV based lentiviral vectors, we have developed a BIV based gene transfer system. To our best knowledge, BIV is not a human pathogen and does not cause any obvious disease in its natural host.

BIV has not been intensively studied. For example, the packaging signal had not been identified. As a consequence, in some prior constructs, both packaging and vector transcripts were packed into vector particles, resulting in lower titer BIV lentiviral vector. In this example, we deleted a putative packaging sequence the region from the MSD to the gag start codon. We found that this sequence is part of the BIV packaging signal (data not shown). We have also found that the upstream sequence of MSD and the first 200 bp of gag contain the additional elements for efficiently packaging BIV transcript.

We have determined the approximate titer of our current BIV lentiviral vector using a vector encoding puromycin resistant selection marker. The BIV vector titer achieved approximate $1.2\times10^6$ infectious units per ml, which is comparable with HIV based lentiviral vectors. We have also determined that the VSV-G pseudotyped BIV lentiviral vector can be concentrated to a higher titer with a simple ultracentrifugation step.

We have also confirmed that our BIV based lentiviral vector indeed is able to integrate into cellular chromosome, resulting long-term sustained gene expression as indicated by Southern blot analysis and continuous passage of BIV transduced human cells.

Skeletal muscle cells represent ideal targets for human gene therapy especially for secretory therapeutic proteins as it is easy to administrate an agent intramuscularly. In this study, we transduced both dividing and non-dividing human primary skeletal muscle cells. We found our nonconcentrated BIV based lentiviral vector efficiently transduced these cells.

Example 6.6

Summary

Lentiviral based gene transfer systems represent a promising gene delivery technology due to their ability to efficiently transduce a variety of non-dividing target cells in vitro and in vivo. Incorporation into the cellular chromosome results in long term transgene expression. In addition, lentiviral vector-mediated gene expression does not require de novo synthesis of viral protein, reducing the potential elimination of target cells by the host immune system. However, the lentivirus systems with the most promising results to date are those based on HIV. HIV is the causative agent of AIDS. Several animal lentivirus based gene transfer systems have been developed. Although these systems provide alternatives to HIV based vectors, the titer and transduction efficiency from animal lentiviral vectors are lower comparing to HIV based vectors. In this example, we described an improved BIV based lentiviral vector system which achieved a titer $1\times10^6$ i.u./ml (infectious units per ml) (nonconcentrated) and can be concentrated more than 150 fold. BIV based lentiviral vectors efficiently transduce both dividing and non-dividing human skeletal muscle cells. Our data indicate that BIV based lentiviral vector may provide an excellent gene transfer system for human gene therapy.

Example 7

Generation of a Minimal BIV Based Lentiviral Vector System

A desired minimal BIV based lentiviral vector system consists of a minimal vector construct, a minimal packaging construct, and a viral surface protein expression vector construct.

Example 7.1

Minimal Vector Construct

Figure 5:
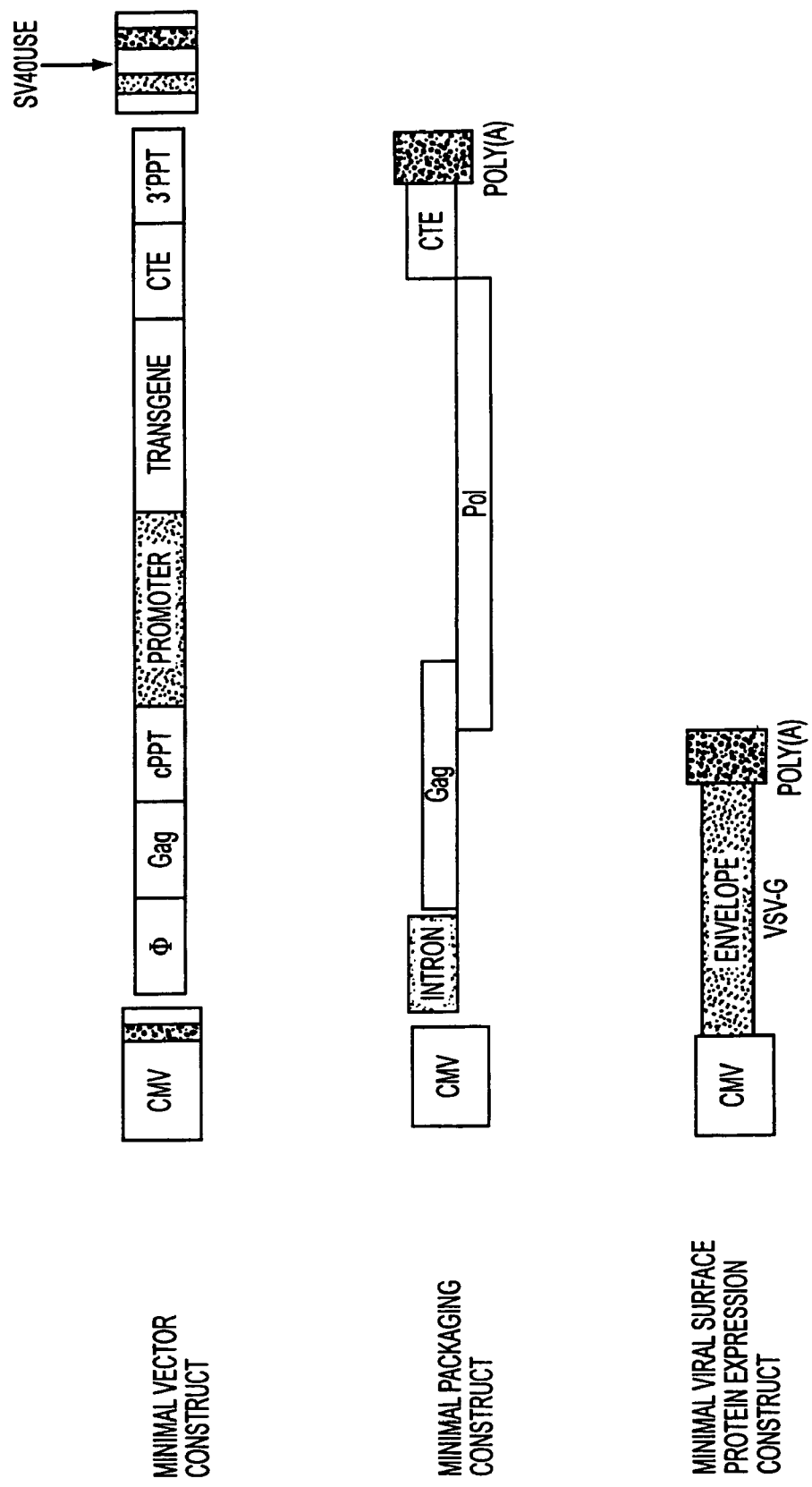
FIG. 5: A minimal BIV based vector system. The figure shows a minimal vector construct, a minimal packaging construct, and a minimal viral surface protein expression construct.

A minimal BIV based vector (designated BC4MG.min) contains a modified BIV 5' LTR, mutated major splicing donor site, packaging sequence, minimal gag sequence, cPPT, a transgene operably linked to an internal promoter, CTE (constitutive transport element from Mason-Pfizer monkey virus), 3' PPT, and modified 3' LTR. See FIG. 5. Specifically, the CMV-immediate-early promoter, ending in the TATA box is linked to the BIV 5' LTR starting immediately after TATA box. BIV sequences terminate at 200 bp into gag coding region. All vectors contain a reporter gene or other transgene cDNA linked to a heterologous, internal promoter: CMV, PGK, or MND. Downstream of the transgene cDNA lies the BIV 3' LTR and 80 bp of adjacent env sequences that contains a 3' PPT. A putative cPPT is inserted upstream of the internal promoter and one or multiple copies of CTE is inserted downstream of the transgene. The 3' LTR contains a large deletion in the U3 region and an insertion of SV40 late polyadenylation signal upstream enhancer element as described in Example 1.

The minimal BIV based vector is generated on the basis of BC4MGppt with the following modifications: (i) further deletion of gag sequence to 200 bp; (ii) mutation of gag start codon ATG; (iii) mutation of the major splicing donor site (MSD); and (iv) replacement of the putative BIV rev-response element (RRE) with a CTE.

To facilitate the plasmid manipulation, the BC4MGppt is digested with BspMI, and the resulting 4743 bp fragment containing the entire vector sequence is cloned into pBluescript previously digested with HincII, giving rise to BS4MGppt.

To make a further deletion on gag sequence, BS4MGppt is digested with EcoNI and BglII, the resulting 7287 bp fragment is self ligated to make plasmid BS4MGppt.Δgag. The resulting vector contains only a 200 bp BIV gag sequence.

To mutate the major splicing donor site, plasmid BS4MGppt.Δgag from the upsteam of the CMV promoter region to the MSD region is PCR amplified with primers MSD5 (5'-GCTCTAGAACTAGTGGATCCCCCG-GCATCCCG-3') and MSD3 (5'-GGGGAAAACACG-CAACTTCTCTCCTGTCCGGAG-3'). The amplified product is digested with SpeI and SmaI and ligated into the 6373 bp fragment resulting from BS4MGppt.Δgag previously digested with SpeI and SmaI. The resulting plasmid is named BS4MGppt.ΔMSD.

To make a mutation in the gag start codon, plasmid BS4MGpptΔMSD from the upstream of the CMV promoter region to the gag region is PCR amplified with primers gag5 (5'-TCTAGAACTAGTGGATCCCCC-3') and gag3 (5'-CTCTTCAACCCGGGGAAAAC-3'). The amplified product is digested with SpeI and SmaI and ligated into the 6373 bp fragment resulting from BS4MGppt.Δgag previously digested with SpeI and SmaI. The resulting plasmid is designated BS4MGppt.ΔgagATG.

To replace the putative BIV rev-response element (BIVRRE) with CTE, a CTE sequence is inserted into SspBI site of plasmid BS4MGppt.ΔgagATG and followed by complete removal of the BIVRRE. To insert the CTE, the Mason-Pfizer Monkey Virus CTE (MPMV CTE) is PCR amplified with primers CTE5' (5'-TGATCTGTACAAG-TAAGCTAGCACCTCCCCTGTGAG-3') and CTE3' (5'-CCTTTTGTACAGTCGACATGCATGACACATCCC-3'). The amplified product is digested with SspBI and ligated into BS4MGppt.ΔgagATG digested with SspBI. The resulting plasmid is named BS4MGpptCTE.ΔgagATG. To remove BIVRRE, first, the upstream of the BIVRRE is subjected to PCR amplification with primers RRE1 (5'-GTTGGCGC-CCAACGTGGGGCTCGAGTAAGAGAG-3') and RRE2 (5'-TAAGTGACCTATTTCTTCAGTGGTGTGTGT-3') while the downstream of the BIVRRE is subjected to PCR amplification with primers RRE3 (5'-ATAGGTCACT-TATATGGGAATGAAGACCC-3') and RRE4 (5'-AACT-GCTGAGGGCGGGACCGCATCTGG-3'). Second, the two amplified products are mixed and subjected to PCR amplification with primers RRE1 and RRE4. The final product is digested with KasI and BbvCI and ligated to plasmid BS4MGpptCTE.ΔgagATG previously digested with KasI and BbvCI, generating a minimal BIV based vector construct, BS4MG.min Example 7.2

Minimal Packaging Construct

A minimal packaging construct contains BIV gag and pol coding sequences linked to one or multiple copies of a CTE. See FIG. 5.

To generate the minimal packaging construct, first, CTE is PCR amplified with two primers CTE1 (5'-CGGGGTAC-CACCTCCCCTGTGAGCTAG-3') and CTE2 (TGCTCTA-GAGACACATCCCTCGGAGGC-3'). The amplified product is digested with KpnI and XbaI and ligated to a pCI plasmid previously digested with KpnI and XbaI, generating pCI.CTE. Second, BIV gag and pol coding sequence is PCR amplified with two primers GAG5 (5'-CCGCTCGAGAT-GAAGAGAAGGGAGTTAGAA-3') and POL3 (5'-CCGCTCGAGTCACGAACTCCCATCTTGGAT-3'). The amplified product is digested with XhoI and ligated to pCI.CTE previously digested with XhoI, generating a minimal BIV based packaging construct, BIVGPCTE.

Example 7.3

Expression Vector Construct

The minimal BIV based lentiviral vector system further contains a third construct, an expression vector construct comprising a gene encoding a viral envelope protein from a different virus. The viral surface protein may be any other viral envelope protein including vesicular stomatitis virus envelope glycoprotein (VSV-G) and others. See FIG. 5.

The disclosures of all patents, publications (including published patent applications), depository accession numbers, and database accession numbers are incorporated herein by reference to the same extent as if each patent, publication, depository accession number, and database accession number were specifically and individually incorporated by reference.

It is understood, however, that the scope of the present invention is not to be limited to the specific embodiments described above. The invention may be practiced other than as particularly described and still be within the scope of the accompanying claims.

What is claimed is:

1. A BIV vector construct comprising:
   a) a DNA segment from a BIV genome;
   b) a packaging sequence to package RNA into virions;
   c) a first promoter operably linked to the DNA segment; and
   d) a transgene operably linked to a second promoter, wherein at least one of vpw, vpy and tat is deleted from said construct.

2. The BIV vector construct of claim 1 wherein the packaging sequence is a BIV packaging sequence.

3. The BIV vector construct of claim 1 wherein said first promoter is an LTR promoter.

4. The BIV vector construct of claim 1 wherein said first promoter is a CMV promoter.

5. The BIV vector construct of claim 1 wherein the transgene is operably linked to a CMV promoter, a PGK promoter, or an MND promoter.

6. The BIV vector construct of claim 1 wherein the DNA segment further comprises a portion of a gag gene.

7. The BIV vector construct of claim 1 further comprising a rev-response element (RRE).

8. The BIV vector construct of claim 1 further comprising a human interferon-beta scaffold attachment region (SAR).

9. The BIV vector construct of claim 1 further comprising a central polypurine tract (cPPT).

10. A vector construct comprising:
    a promoter linked to a first BIV R region;
    a BIV U5 element linked to the first BIV R region;
    a packaging sequence;
    a transgene; and
    a BIV U3 element linked to a second BIV R region, wherein the promoter initiates RNA transcription of the vector construct, and at least one of vpw, vpy and tat is deleted from said construct.

11. The vector construct of claim 10, wherein the transgene is operably linked to an internal promoter.

12. The vector construct of claim 10, wherein one or more nucleotides in the U3 element are mutated or deleted to diminish or eliminate U3-mediated transcription.

13. The vector construct of claim 10, wherein the packaging sequence is a BIV packaging sequence.

14. The vector construct of claim 10, wherein any start codons in the packaging sequence are eliminated by deletion or mutation.

15. The vector construct of claim 10, wherein the U3 element further comprises a sequence that enhances polyadenylation.

16. The vector construct of claim 10, further comprising a cPPT.

17. The vector construct of claim 16, wherein the cPPT is a BIV cPPT.

18. The vector construct of claim 10, further comprising a 3' polypurine tract.

19. The vector construct of claim 10, further comprising an RNA transport element.

20. The vector construct of claim 19, wherein the RNA transport element is a lentiviral rev response element (RRE).

21. The vector construct of claim 20, wherein the lentiviral RRE is a BIV RRE.

22. The vector construct of claim 19, wherein the RNA transport element is a constitutive transport element (CTE).

23. The vector construct of claim 22, wherein the CTE is a Mason-Pfizer Monkey Virus CTE.

24. A cell comprising a BIV vector construct comprising:
    a) a DNA segment from a BIV genome,
    b) a packaging sequence to package RNA into virions,
    c) a first promoter operably linked to the DNA segment, and
    d) a transgene operably linked to a second promoter, wherein at least one of vpw, vpy and tat is deleted from said construct.

25. The cell of claim 24, wherein said packaging sequence is a BIV packaging sequence.

26. The cell of claim 24, wherein said first promoter is an LTR promoter.

27. The cell of claim 24, wherein said first promoter is a CMV promoter.

28. The cell of claim 24, wherein said transgene is operably linked to a CMV promoter, a PGK promoter or an MND promoter.

29. The cell of claim 24, wherein said DNA segment further comprises a portion of a gag gene.

30. The cell of claim 24, wherein said construct further comprises a rev-response element (RRE).

31. The cell of claim 30, wherein said RRE is a BIV RRE.

32. The cell of claim 24, wherein said construct further comprises a human interferon-beta scaffold attachment region (SAR).

33. The cell of claim 24, wherein said construct further comprises a central polypurine tract (cPPT).

34. The cell of claim 24, wherein said construct comprises a portion of a U3 region of a BIV 3' LTR.

35. The cell of claim 34, wherein a portion of said U3 region of a 3' LTR is deleted or replaced by a heterologous sequence.

36. A cell comprising a vector construct comprising:
    a promoter linked to a first BIV R region;
    a BIV U5 element linked to the first BIV R region;
    a packaging sequence;
    a transgene; and
    a BIV U3 element linked to a second BIV R region, wherein the promoter initiates RNA transcription of the vector construct, and at least one of vpw, vpy and tat is deleted from said construct.

37. The cell of claim 36, wherein said transgene is operably linked to an internal promoter.

38. The cell of claim 36, wherein one or more nucleotides in said U3 element are mutated or deleted to diminish or eliminate U3-mediated transcription.

39. The cell of claim 36, wherein said packaging sequence is a BIV packaging sequence.

40. The cell of claim 36 wherein any start codons in said packaging sequence are eliminated by deletion or mutation.

41. The cell of claim 36, wherein said U3 element further comprises a sequence that enhances polyadenylation.

42. The cell of claim 36, wherein said construct further comprises a major splice donor site.

43. The cell of claim 42, wherein said major splice donor site has been inactivated or eliminated.

44. The cell of claim 36, wherein said vector further comprises a cPPT.

45. The cell of claim 44, wherein said cPPT is a BIV cPPT.

46. The cell of claim 36, wherein said vector further comprises a 3' polypurine tract.

47. The cell of claim 36, wherein said vector further comprises an RNA transport element.

48. The cell of claim 47, wherein said RNA transport element is a lentiviral rev response element (RRE).

49. The cell of claim 48, wherein said lentiviral RRE is a BIV RRE.

50. The cell of claim 47, wherein said RNA transport element is a constitutive transport element (CTE).

51. The cell of claim 50, wherein said CTE is a Mason-Pfizer Monkey Virus CTE.

52. The BIV vector construct of claim 7, wherein said RRE is a BIV RRE.

53. The BIV vector construct of claim 1, further comprising a portion of a U3 region of a BIV 3' LTR.

54. The vector construct of claim 10, further comprising a major splice donor site.

55. The BIV vector construct of claim 53, wherein a portion of the U3 region of the 3' LTR is deleted or replaced by a heterologous sequence.

56. The vector construct of claim 54, wherein the major splice donor site has been inactivated or eliminated.

* * * * *

SEQUENCE LISTING

```
<160> NUMBER OF SEQ ID NOS: 30

<210> SEQ ID NO 1
<211> LENGTH: 28
<212> TYPE: DNA
```

```
<213> ORGANISM: Artificial Sequence
<220> FEATURE:
<223> OTHER INFORMATION: restriction site polylinker
<220> FEATURE:
<221> NAME/KEY: misc_feature
<222> LOCATION: (1)..(28)
<223> OTHER INFORMATION: restriction site polylinker

<400> SEQUENCE: 1
ttaagattta aatacgcgtg cggccgca                                              28

<210> SEQ ID NO 2
<211> LENGTH: 28
<212> TYPE: DNA
<213> ORGANISM: Artificial Sequence
<220> FEATURE:
<223> OTHER INFORMATION: restriction site polylinker
<220> FEATURE:
<221> NAME/KEY: misc_feature
<222> LOCATION: (1)..(28)
<223> OTHER INFORMATION: restriction site polylinker

<400> SEQUENCE: 2
gatctgcggc cgcacgcgta tttaaatc                                              28

<210> SEQ ID NO 3
<211> LENGTH: 50
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(50)

<400> SEQUENCE: 3
tatccatacg atgttccaga ttatgcttaa agatagggggg gcaattaaag                     50

<210> SEQ ID NO 4
<211> LENGTH: 46
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(46)

<400> SEQUENCE: 4
agcataatct ggaacatcgt atggatattg tgacgagggg tcgctg                          46

<210> SEQ ID NO 5
<211> LENGTH: 50
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(50)

<400> SEQUENCE: 5
tatccatacg atgttccaga ttatgcttag acaaacagcc ttttataaag                      50

<210> SEQ ID NO 6
<211> LENGTH: 48
<212> TYPE: DNA
<213> ORGANISM: Artificial Sequence
<220> FEATURE:
```

```
<223> OTHER INFORMATION: PCR primer
<220> FEATURE:
<221> NAME/KEY: primer_bind
<222> LOCATION: (1)..(48)

<400> SEQUENCE: 6
agcataatct ggaacatcgt atggataatc taatataaga ggggtgc            48

<210> SEQ ID NO 7
<211> LENGTH: 36
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(36)

<400> SEQUENCE: 7
cgggatcccg tagttattaa tagtaatcaa ttacgg                        36

<210> SEQ ID NO 8
<211> LENGTH: 32
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(32)

<400> SEQUENCE: 8
agatatggtt tatatagacc tcccaccgta ca                            32

<210> SEQ ID NO 9
<211> LENGTH: 33
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(33)

<400> SEQUENCE: 9
gggaggtcta tataaaccat atcttcactc tgt                           33

<210> SEQ ID NO 10
<211> LENGTH: 21
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(21)

<400> SEQUENCE: 10
gccgtttctg tactctctgg t                                        21

<210> SEQ ID NO 11
<211> LENGTH: 19
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(19)
```

<400> SEQUENCE: 11
gaggacggca acatcctgg                                                    19

<210> SEQ ID NO 12
<211> LENGTH: 50
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(50)

<400> SEQUENCE: 12
agcaatagca tcacaaattt cacaaataaa cacatatggg aagtccgggg                  50

<210> SEQ ID NO 13
<211> LENGTH: 54
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(54)

<400> SEQUENCE: 13
gtgaaatttg tgatgctatt gctttatttg taatctgtac ttcagctcgt gtag             54

<210> SEQ ID NO 14
<211> LENGTH: 19
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(19)

<400> SEQUENCE: 14
tcgccgacat caccgatgg                                                    19

<210> SEQ ID NO 15
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(20)

<400> SEQUENCE: 15
cgacccgggc ggccgcttcg                                                   20

<210> SEQ ID NO 16
<211> LENGTH: 20
<212> TYPE: DNA
<213> ORGANISM: Bovine immunodeficiency virus

<400> SEQUENCE: 16
ctactcacct gtccggagtc                                                   20

<210> SEQ ID NO 17
<211> LENGTH: 32
<212> TYPE: DNA

-continued

```
<213> ORGANISM: Artificial Sequence
<220> FEATURE:
<223> OTHER INFORMATION: pcr primer
<220> FEATURE:
<221> NAME/KEY: primer_bind
<222> LOCATION: (1)..(32)

<400> SEQUENCE: 17
gctctagaac tagtggatcc cccggcatcc cg                          32

<210> SEQ ID NO 18
<211> LENGTH: 33
<212> TYPE: DNA
<213> ORGANISM: Bovine immunodeficiency virus

<400> SEQUENCE: 18
ggggaaaaca cgcaacttct ctcctgtccg gag                         33

<210> SEQ ID NO 19
<211> LENGTH: 21
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(21)

<400> SEQUENCE: 19
tctagaacta gtggatcccc c                                      21

<210> SEQ ID NO 20
<211> LENGTH: 20
<212> TYPE: DNA
<213> ORGANISM: Bovine immunodeficiency virus

<400> SEQUENCE: 20
ctcttcaacc cggggaaaac                                        20

<210> SEQ ID NO 21
<211> LENGTH: 36
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(36)

<400> SEQUENCE: 21
tgatctgtac aagtaagcta gcacctcccc tgtgag                      36

<210> SEQ ID NO 22
<211> LENGTH: 33
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(33)

<400> SEQUENCE: 22 cctttttgtac agtcgacatg catgacacat ccc                        33

<210> SEQ ID NO 23
<211> LENGTH: 33
```

```
<212> TYPE: DNA
<213> ORGANISM: Bovine immunodeficiency virus

<400> SEQUENCE: 23
gttggcgccc aacgtggggc tcgagtaaga gag                          33

<210> SEQ ID NO 24
<211> LENGTH: 30
<212> TYPE: DNA
<213> ORGANISM: Bovine immunodeficiency virus

<400> SEQUENCE: 24
taagtgacct atttcttcag tggtgtgtgt                              30

<210> SEQ ID NO 25
<211> LENGTH: 30
<212> TYPE: DNA
<213> ORGANISM: Bovine immunodeficiency virus

<400> SEQUENCE: 25
ataggtcact tatatgggaa tgaaagaccc                              30

<210> SEQ ID NO 26
<211> LENGTH: 27
<212> TYPE: DNA
<213> ORGANISM: Bovine immunodeficiency virus

<400> SEQUENCE: 26
aactgctgag ggcgggaccg catctgg                                 27

<210> SEQ ID NO 27
<211> LENGTH: 27
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(27)

<400> SEQUENCE: 27
cggggtacca cctcccctgt gagctag                                 27

<210> SEQ ID NO 28
<211> LENGTH: 27
<212> TYPE: DNA
<213> ORGANISM: Artificial Sequence
<220> FEATURE:
<223> OTHER INFORMATION: PCR primer
<220> FEATURE:
<221> NAME/KEY: primer_bind
<222> LOCATION: (1)..(27)

<400> SEQUENCE: 28
tgctctagag acacatccct cggaggc                                 27

<210> SEQ ID NO 29
<211> LENGTH: 30
<212> TYPE: DNA
<213> ORGANISM: Bovine immunodeficiency virus

<400> SEQUENCE: 29
ccgctcgaga tgaagagaag ggagttagaa                              30

<210> SEQ ID NO 30
```

```
<211> LENGTH: 30
<212> TYPE: DNA
<213> ORGANISM: Bovine immunodeficiency virus

<400> SEQUENCE: 30
ccgctcgagt cacgaactcc catcttggat                                           30
```